(12) United States Patent
Shazly et al.

(10) Patent No.: US 10,702,338 B2
(45) Date of Patent: Jul. 7, 2020

(54) LASER SYSTEM WITH PULSE MODULATION AND CORRESPONDING METHOD OF USE

(71) Applicant: VISUMEDICS, INC., Reading, MA (US)

(72) Inventors: Tarek A. Shazly, Pittsburgh, PA (US); Mark A. Latina, Reading, MA (US)

(73) Assignee: Visumedics, Inc., Reading, MA (US)

( * ) Notice: Subject to any disclaimer, the term of this patent is extended or adjusted under 35 U.S.C. 154(b) by 520 days.

(21) Appl. No.: 15/296,614

(22) Filed: Oct. 18, 2016

(65) Prior Publication Data

US 2017/0112572 A1 Apr. 27, 2017

Related U.S. Application Data

(60) Provisional application No. 62/246,793, filed on Oct. 27, 2015.

(51) Int. Cl.
*A61B 9/00* (2006.01)
*A61B 18/20* (2006.01)
(Continued)

(52) U.S. Cl.
CPC ............ *A61B 18/203* (2013.01); *A61B 18/20* (2013.01); *A61F 9/00821* (2013.01);
(Continued)

(58) Field of Classification Search
CPC combination set(s) only.
See application file for complete search history.

(56) References Cited

U.S. PATENT DOCUMENTS 4,118,619 A * 10/1978 McArthur .............. A24C 5/007
219/121.7
4,432,511 A * 2/1984 Tong ...................... F41G 7/26
244/3.13
(Continued)

FOREIGN PATENT DOCUMENTS

WO WO 01/78830 A2 10/2001
WO WO 03/086322 A2 10/2003
WO WO 2015/195940 A1 12/2015

OTHER PUBLICATIONS

Notice of Allowance from U.S. Appl. No. 14/743,482; dated Mar. 26, 2018.
(Continued)

*Primary Examiner* — Michael W Kahelin
*Assistant Examiner* — Shirley X Jian
(74) *Attorney, Agent, or Firm* — Morse, Barnes-Brown & Pendleton, P.C.; Sean D. Detweiler, Esq.

(57) ABSTRACT

A method and system for thermal and non-thermal laser treatments includes a visible laser source. A laser beam in the visible spectrum is generated by the visible laser source and produces a modulated laser output. Laser controls allows the user to generate the pulsed output with variable pulse characteristics to provide selective, localized and user controlled thermal and or non-thermal biological effects at a targeted tissues. This laser system modulates the delivered laser energy to produce accurate and selective targeting of the pigmented cells of the treated tissues to induce therapeutic effects via gentle warming of the cells without significant collateral damage to surrounding tissues.

7 Claims, 17 Drawing Sheets

(51) Int. Cl.
    *G02B 26/04*  (2006.01)
    *H01S 3/23*  (2006.01)
    *A61F 9/008*  (2006.01)
    *H01S 3/00*  (2006.01)
    *A61B 18/00*  (2006.01)

(52) U.S. Cl.
    CPC ............ *G02B 26/04* (2013.01); *H01S 3/2391* (2013.01); *A61B 2018/00208* (2013.01); *A61B 2018/00589* (2013.01); *A61B 2018/00642* (2013.01); *A61B 2018/2025* (2013.01); *A61B 2018/2045* (2013.01); *A61B 2018/2055* (2013.01); *A61B 2018/205547* (2017.05); *H01S 3/0085* (2013.01)

(56) References Cited

U.S. PATENT DOCUMENTS

| | | | |
|---|---|---|---|
| 4,499,362 | A | 2/1985 | Martin |
| 4,580,557 | A | 4/1986 | Hertzmann |
| 4,653,478 | A * | 3/1987 | Nagasaki ................. A61B 1/05 348/70 |
| 4,795,256 | A * | 1/1989 | Krause ................... G01J 3/427 356/318 |
| 5,982,789 | A | 11/1999 | Marshall et al. |
| 6,090,102 | A | 7/2000 | Telfair et al. |
| 6,451,008 | B1 | 9/2002 | Frey et al. |
| 6,530,918 | B1 | 3/2003 | Ueno et al. |
| 6,747,244 | B1 * | 6/2004 | Koide ................ B23K 26/0624 219/121.71 |
| 7,115,120 | B2 | 10/2006 | Lin |
| 7,771,417 | B2 | 8/2010 | Telfair et al. |
| 7,894,125 | B2 * | 2/2011 | Langdon ................. G02F 1/116 359/308 |
| 7,949,019 | B2 * | 5/2011 | Bouma ..................... G01J 3/02 372/102 |
| 8,394,076 | B2 | 3/2013 | Latina |
| 8,574,224 | B2 | 11/2013 | Shazly et al. |
| 2003/0179344 | A1 | 9/2003 | Van De Velde |
| 2004/0039378 | A1 | 2/2004 | Lin |
| 2004/0116909 | A1 | 6/2004 | Neuberger et al. |
| 2004/0158300 | A1 * | 8/2004 | Gardiner .............. A61N 5/0619 607/88 |
| 2005/0143720 | A1 | 6/2005 | Yamada et al. |
| 2005/0203593 | A1 | 9/2005 | Shanks et al. |
| 2005/0240168 | A1 | 10/2005 | Neuberger et al. |
| 2006/0187978 | A1 | 8/2006 | Telfair et al. |
| 2007/0030563 | A1 * | 2/2007 | Zueger .................. G02B 5/208 359/359 |
| 2007/0121069 | A1 | 5/2007 | Andersen et al. |
| 2007/0213693 | A1 | 9/2007 | Plunkett |
| 2008/0015553 | A1 | 1/2008 | Zacharias |
| 2008/0108983 | A1 | 5/2008 | Nadolski |
| 2008/0175280 | A1 * | 7/2008 | Bouma ..................... G01J 3/02 372/20 |
| 2008/0252851 | A1 | 10/2008 | Shazly et al. |
| 2008/0269847 | A1 | 10/2008 | Nemenov |
| 2009/0195852 | A1 * | 8/2009 | Bassler ................ G01N 21/645 359/238 |
| 2009/0284826 | A1 * | 11/2009 | Langdon ................. G02F 1/116 359/308 |
| 2010/0318074 | A1 | 12/2010 | Dacquay et al. |
| 2011/0075104 | A1 | 3/2011 | Sakakibara |
| 2011/0098692 | A1 | 4/2011 | Shazly et al. |
| 2011/0306919 | A1 | 12/2011 | Latina et al. |
| 2013/0237972 | A1 | 9/2013 | Raksi |
| 2013/0261612 | A1 | 10/2013 | Yokosuka et al. |
| 2013/0338649 | A1 | 12/2013 | Hanebuchi et al. |
| 2013/0345683 | A1 | 12/2013 | Mordaunt et al. |
| 2014/0121631 | A1 | 5/2014 | Bean et al. |
| 2014/0228824 | A1 | 8/2014 | Yee et al. |
| 2014/0243805 | A1 | 8/2014 | Dick et al. |
| 2015/0366713 | A1 | 12/2015 | Shazly et al. |

OTHER PUBLICATIONS

International Search Report for International Application No. PCT/US2016/057500, dated Feb. 24, 2017.

Non-Final Office Action received in U.S. Appl. No. 14/743,482, dated Sep. 29, 2017.

International Search Report for International Application No. PCT/US10/053013, dated Dec. 6, 2010.

International Search Report for International Application No. PCT/US2015/36469, dated Sep. 29, 2015.

* cited by examiner

LASER SYSTEM WITH PULSE MODULATION AND CORRESPONDING METHOD OF USE

CROSS-REFERENCE TO RELATED APPLICATION(S)

This application claims priority to, and the benefit of, U.S. Provisional Application No. 62/246,793, filed Oct. 27, 2015, for all subject matter common to both applications. The disclosure of said provisional application is hereby incorporated by reference in its entirety.

FIELD OF THE INVENTION

The present invention relates to laser systems, and their methods of use, that produce controllable, modulated, variable pulse width trains. In particular, the present invention relates to laser systems, and their methods of use, that produce modulated pulse trains of visible laser of the appropriate pulse length, duty cycle, and power to perform both thermal and non-thermal laser treatments.

BACKGROUND

Generally, laser photocoagulation has been the standard treatment of a number of ocular and non-ocular disorders. In particular, ocular disorders such as proliferative diabetic retinopathy (PDR), diabetic macular edema (DME), choroidal neovascularization (CNV), retinal tears, and retinal vein occlusion (RVO) can be successfully managed using laser photocoagulation. Additionally, laser photocoagulation has been successfully used for treatment of cutaneous vascular and pigmented lesions. Retinal laser photocoagulation settings utilized for ocular treatments, indications, and outcomes of the treatments have been well evaluated by multiple national trials such as the diabetic retinopathy study (DRS), the early treatment of diabetic retinopathy study (ETDRS), and the macula photocoagulation study (MPS). The vast majority of these studies were conducted utilizing visible lasers, particularly in the green range produced by Argon or Krypton gas lasers. All of these studies provided evidence for the beneficial use of lasers in preserving vision and treating ocular disorders.

Generally, photocoagulation involves heating up the tissues to produce irreversible cellular damage to decrease the metabolic demand of the tissues. This is achieved by irradiating the tissues with a high fluence of laser radiation, that in turn is absorbed by the by tissue chromophores, most significantly melanin. The chromophores build up heat that diffuses to surrounding tissues to cause photocoagulation of the adjacent tissues. All of the above laser treatments involve longer pulses of a continuous wave (CW) laser to photocoagulate the tissues, typically for 50 milliseconds or longer. A progressive rise in tissue temperature in laser photocoagulation is caused when the rate of tissue temperature rise exceeds that of heat dissipation, which does not allow for cooling down of tissues.

Ophthalmic laser treatments have been shown to result in therapeutic effects without causing irreversible photocoagulative damage to the ocular tissues. This non-photo-coagulative therapeutic effect can be obtained utilizing short-pulsed lasers as discussed in the early work by Pankratov, "Pulsed delivery of laser energy in experimental thermal retinal photocoagulation", Proc. SPIE, V1202, pp. 205-213, 1990, wherein it is suggested that when the laser was pulsed in the frequency range of 1-20 kHz, the most influential factor determining the size of the laser burn was the duty cycle. Pankratov reported that the smaller the duty cycle, the smaller the lesion. The short pulse laser treatments have demonstrated beneficial effects while minimizing deep choroidal damage by using a pulse train with a low duty cycle to confine the thermal effects to the cells with the chromophores.

Q-switched lasers are capable of producing very short laser pulses, typically in the range of 3-10 nanoseconds. Q-switched lasers have been used for selective laser trabeculoplasty (SLT) treatment of the trabecular meshwork for treatment of glaucoma and selective retinal treatment (SRT) for clinically significant diabetic macular edema (CSME) via selectively targeting the melanophores within the trabecular meshwork and the retinal pigment epithelium (RPE) respectively. However, the use of such short pulses with very high max power over a very short period of time results in plasma formation causing photo disruption and mechanical shock wave in the targeted tissues. This process can cause bubbling and mechanical damage of the targeted tissue.

Sub-lethal laser treatments can be performed either with a long, CW, low energy level laser treatment, or via a CW laser with short and controlled pulse widths. Low-level laser therapy (LLLT) using low level laser (LLL) is a non-thermal medical laser treatment modality commonly used with photo-bio-modulation. LLLT has become an increasingly used laser modality. While LLLT has been used mainly for wound healing and pain relief, the medical applications of LLLT have broadened to include diseases such as stroke, myocardial infarction, and degenerative or traumatic brain disorders. For example, in 1967, Endre Mester noticed the ability of the low power Helium-neon (HeNe) laser to increase hair growth and stimulate wound healing in mice (Mester E, Spiry T, Szende B, et al. Effect of laser rays on wound healing. Am J Surg. 1971; 122:532-535.).

There are different protocols for LLLT but the common features include irradiating the tissues with a visible or infrared laser of low fluence of 10 $mW/cm^2$–0.5 $W/cm^2$. LLLT acts by inducing a photochemical reaction in the tissues at a cellular level. LLLT has multiple recognized modes of action, most prominently the ability to reduce inflammation. In particular, LLLT produces an anti-inflammatory effect via lowering levels of prostaglandin E2, prostaglandin-endoperoxide synthase 2, interleukin 1-beta, tumor necrosis factor-alpha, and the cellular influx of neutrophil granulocytes, oxidative stress, edema, and bleeding. The appropriate dose for LLLT has been suggested to be between 0.3 and 19 joules/$cm^2$ (Bjordal, J. M.; Johnson, M. I.; Iversen, V.; Aimbire, F.; Lopes-Martins, R. A. B. (2006). "Low-Level Laser Therapy in Acute Pain: A Systematic Review of Possible Mechanisms of Action and Clinical Effects in Randomized Placebo-Controlled Trials". Photomedicine and Laser Surgery 24 (2): 158-68. doi:10.1089/pho.2006.24.158).

Alternative to LLLT, there are lasers that generate a pulse train of short pulses (typically 100 to 10,000 microseconds) with higher power during the pulse, but significant off time between pulses (typically 5 to 25% ON duty cycle and 75-95% OFF). This allows the energy to be confined in a small area using the thermal dissipation principle. The thermal confinement results in focal and localized therapeutic effect because the specific absorbing tissue, which is being heated by the pulses to temperatures above the standard photocoagulation threshold, are activated but not irreversibly coagulated; since the heat can dissipate fast enough that no coagulation takes place. This method allows significant treatment without causing full thickness retinal damage and the associated vision loss.

Currently available lasers for retinal laser treatments include visible green, green-yellow, yellow or red lasers that are obtained via diode pumped solid state (DPSS) laser sources. The standard DPSS photocoagulator lasers require continuous and fast sensing of the actual laser output power level of the laser cavity using a photodetector and feedback current control mechanisms because of the fluctuation of the laser output with the change of the temperature of the laser pumping diode, laser gain medium, and frequency doubling crystal.

DPSS lasers, unlike diode lasers, are very susceptible to variations in the output power of the pumping diode. This variation is due to a number of reasons, but two of the reasons are particularly important: 1) The laser gain medium and the second harmonic conversion crystal are both optically non-linear in response to their respective excitation wavelengths, therefore alterations in the original pump diode output power can lead to unexpected effects including unstable performance and increased optical noise; and, 2) The thermo-mechanical stability of the DPSS laser is controlled very carefully to ensure stable optical performance, varying the pump diode power can affect this thermal equilibrium to the detriment of the laser performance and lifetime. Additionally, despite active temperature management of the different components of the DPSS cavity, the temperature control is much slower than the fluctuation of cavity component temperature. Moreover, all DPSS lasers, regardless of the wavelength, have limited modulation speed. Furthermore, DPSS sources when compared to laser diodes are well known for their low power efficiency, high sensitivity to temperature, and the need for active cooling, complexity, larger size, and weight, progressive loss of power, higher cost, and shorter life span.

Recently, short pulsed visible lasers have become available in both green (532 nm) and yellow (577 nm) through a DPSS source controlled with software and/or hardware control loops (see U.S. Pat. No. 7,771,417). The software control loop, in response to the signal from the photodetector, alters drive current to the visible laser diode within about a millisecond, and the hardware control loop, in response to the signal from the photodetector, controls timing of the train of pulses to within a microsecond. The DPSS controller provides instructions for the output of the train of pulses with on times of 25 microseconds to 10 milliseconds per pulse, such that the train of pulses is sufficient for photoactivation of a therapeutic healing response in tissue at a target site and off times of 31.67 to 100,000 microseconds, such that the train of pulses is insufficient to induce traditional photocoagulation of the tissue at the target site. Additionally, the photodetector couples the controller to the pulsed output so that a power of the pulsed output is within less than 10% of a desired power level.

Additionally, the present invention assumes that the therapeutic effect of the non-thermal lasers is related to the sub-lethal tissue heating from pre-treatment temperature to post-treatment temperature, which triggers the cascade of processes responsible for tissue healing. Despite the lack of lethal damage caused by excessive tissue heating, the heat dissipated from the tissue chromophores causes intracellular warming that can be gradually additive at the cellular level, but not enough to raise the cellular temperature above the critical level of photocoagulation of the cellular proteins. More laser energy is required initially to raise the tissue temperature from the baseline temperature to the desired subcritical temperature. Once the cellular temperature is within the required temperature range, less laser energy is required to maintain temperature to avoid reaching the critical temperature leading to irreversible tissue damage. The currently available non-photocoagulative laser treatments allow laser pulses with fixed energy, fluence, frequency and duty cycle during the on time of laser pulses. Modulating the delivered laser energy to allow for variable laser energy levels per pulse allows optimization of the therapeutic An alternative method of creating a pulsing a continuous wave (CW) beam is through optical chopping. Traditionally, optical chopping usually involves a rotating disc punctuated with radially arranged holes or slits. As the disc rotates at a certain speed, it periodically blocks the beam and thus pulses the laser at a fixed frequency and fixed duty cycle. The optical chopper is typically driven by an electronic controller which allows for precise control of the rotational frequency of the disc. Because optical choppers are mechanical in nature, the maximum frequency is limited to the high kHz domain, due mainly to air resistance restricting the speed of the optical chopper. The diameter of the laser beam also places some constraints on the size of the slits, and therefore the maximum pulse frequency is lower for larger diameter beams. Optical chopping allows consistent and clean pulse shape while the laser source is running at CW conditions. However, the main limiting factor for pulsing the CW laser for selective tissue targeting, is the inability to change the duty cycle without physically adjusting the rotating disc.

SUMMARY

There is a need for a surgical laser system that can be used in ophthalmology, dermatology, vascular surgery, as well as other medical and surgical applications that operates at a wavelength that is effective for a variety of treatments with user controllable laser power modulation. The present invention is directed toward further solutions to address this need, in addition to having other desirable characteristics.

Accordingly, the present invention provides an improved system, and its methods of use, that produces user adjustable laser with short pulse width trains to produce favorable biological responses. In particular, the present invention provides a visible laser including short and controlled pulse width trains, and its methods of use, include variable duty cycles within the pulse envelope. In particular, the visible laser produces high frequency short and controlled pulse width trains, and its methods of use, include variable duty cycles within the pulse envelope. The use of the same laser source for aiming and treatment allows shortening of the rise time by running the laser source at a sub-threshold level for aiming. For example, the visible laser system and its methods of use deliver pulse rise times as short as 20 microseconds, pulse lengths in the 1.67 microseconds to 10 milliseconds range, and pulse trains of these pulses for hundreds to thousands of pulses.

In accordance with an example embodiment of the present invention, the visible laser produces the short and controlled pulses that are modulated to produce alternating power level, and methods of use, with variable power level and duty cycles. The short and controlled pulse width trains of the visible laser are produced with reduced power fluctuations (e.g., fluctuations less than 5%).

In accordance with aspects of the present invention, the visible laser has two laser power outputs, namely, a first continuous low laser power with superimposed laser trains to minimize excessive temperature fluctuation of the tissues.

In accordance with aspects of the present invention, the visible laser that produces three laser output levels: an aiming level for aiming of the laser beam, a low continuous wave level of low power insufficient to cause coagulative damage but enough to stimulate the tissues, and controlled pulse width trains of higher power level, and its methods of use. Such a system is provided with a minimum of moving parts and a minimum of complexity.

In accordance with an example embodiment of the present invention, there is provided an apparatus for converting a continuous incident laser beam into a pulsed output beam with ON periods alternating with OFF periods, with the duty cycle of the beam substantially continuously variable between minimum and maximum values.

In accordance with an example embodiment of the present invention, an apparatus is provided for converting a continuous incident laser beam into a pulsed output beam with high power periods alternating with low power periods, with the duty cycle of the beam substantially continuously variable between minimum and maximum values.

In accordance with an example embodiment of the present invention, the system and method further provide a mechanical rotary chopper system for interrupting a continuous laser beam, wherein the duty cycle may be substantially continuously varied between a minimum value and a maximum value that can be adjusted without disassembling the chopper.

These and other objects of the present invention are achieved in a laser system that includes a visible laser source. The visible laser is directly generated by the visible laser source and produces a pulsed laser output via electric current modulation (at a given voltage) or mechanical chopping of the beam resulting in a train of pulses. Resources provide instructions for the creation of the pulsed output, with on and off times that provide for substantial confinement of thermal effects at a target site.

In accordance with an example embodiment of the present invention, a system for performing laser treatments includes a diode laser assembly having at least one laser diode source configured to produce a controllable laser beam. A driving control unit provides the at least one laser diode source with three different power settings including an aiming level power setting causing generation of an aiming laser beam, a low level power setting that is greater than the aiming level power setting and causes generation of a continuous low-level laser (LLL) beam for warming target tissues without causing photocoagulation, and a high level power setting that has an upper level power setting greater than the low level power setting and causes generation of a high level therapy controlled pulse width train laser beam. A laser output assembly directs and focuses output of the controllable laser beam. The at least one laser diode source generates a controllable laser beam output designated by the three different power settings. The controllable laser beam output includes controlled pulse width trains alternating between the LLL beam and a high level therapy laser beam suitable for treating target tissues. The controllable laser beam output further includes emitting the high level therapy controlled pulse width train laser beam in the range of 5 μsec to 100 usec time duration between each pulse. The high level power of the high level therapy controlled pulse width train laser beam is of sufficient power to cause photocoagulation of tissue, but the controllable laser beam output does not cause significant collateral photocoagulation damage to other tissues surrounding the target tissues. The three different power settings are adjusted by adjusting electrical current levels.

In accordance with aspects of the present invention, two laser diode sources can be provided, wherein a first of the two laser diode sources is operable for aiming and a second of the two laser diode sources is operable to alternate between the LLL beam and the high level therapy laser beam during treatment. The first of the two laser diode sources can be controlled by the aiming level setting for aiming a laser beam and the second of the two laser diode sources can be controlled by the low level power setting and the high level power setting. The high level therapy controlled pulse width train laser beam can be controlled by mechanically chopping the output of the controllable laser beam. The controllable laser beam output can be delivered in pulses shorter than a time constant of an absorbing target tissue.

In accordance with an example embodiment of the present invention, a method for producing and controlling a continuous laser beam with short and controlled pulse width trains with variable duty cycles includes provisioning laser pulse parameters. By at least one laser diode source, a controllable laser beam is produced based on the laser pulse parameters. By a driving control unit, the at least one laser diode source is provided with three different power settings comprising an aiming level power setting causing generation of an aiming laser beam, a low level power setting that is greater than the aiming level power setting and causes generation of a continuous low-level laser (LLL) beam for warming target tissues without causing photocoagulation, and a high level power setting that has an upper level power setting greater than the low level power setting and causes generation of a high level therapy controlled pulse width train laser beam. The continuous laser beam is aimed at a treatment area using the aiming laser beam. The continuous laser beam is activated for treatment. By the at least one laser diode source, a controllable laser beam output is generated designated by the three different power settings. The high level therapy controlled pulse width train laser beam alternates between the LLL beam and a high level therapy laser beam suitable for treating target tissues. The high level power of the high level therapy controlled pulse width train laser beam is of sufficient power to cause photocoagulation of tissue, but the controllable laser beam output does not cause significant collateral photocoagulation damage to other tissues surrounding the target tissues. The three different power settings are adjusted by adjusting electrical current levels at a given voltage.

In accordance with aspects of the present invention, during the aiming, a single laser diode can deliver the aiming laser beam continuously through the aiming level power setting. During the treatment, the single laser diode can deliver the high level power setting including the high level therapy controlled pulse width train laser beam alternating between the LLL beam and the high level therapy laser beam suitable for treating target tissues. The high level therapy laser beam can provide the photocoagulation of tissue with an output level of 50 mW to 3000 mW. The LLL beam can gently warm and stimulate target tissues without causing photocoagulation with pulse duration output levels of 1 mW to 49 mW.

In accordance with an example embodiment of the present invention, a system for modulating a laser beam using an optical chopper includes at least one rotating disc including at least one barrier and at least one aperture. The laser beam is positioned perpendicular to the at least one rotating disc. The at least one barrier interrupts the laser beam and the at least one aperture allows the laser beam to pass through the at least one rotating disc uninterrupted to output a high level therapy controlled pulse width train laser beam. The high level therapy controlled pulse width train laser beam is controlled by a speed of rotation and distance from a center of rotation of the at least one rotating disc to mechanically chop the laser beam. A variable duty cycle is determined and controlled by displacement of the at least one rotating disc relative to a path of the laser beam. The at least one barrier completely blocks the laser beam so that the laser beam peaks at a high therapy power level when the laser beam passes through the at least one rotating disc uninterrupted and is OFF when the at least one barrier interrupts the laser beam.

In accordance with aspects of the present invention, the at least one barrier can partially block the laser beam so that the laser beam peaks at a high therapy power level when the laser beam passes through the at least one rotating disc uninterrupted and alternates to a low-level laser therapy power level when the at least one barrier partially interrupts the laser beam. The at least one barrier can include attenuation barriers of variable size in such a way that displacement of the laser beam vertically relative to the at least one rotating disc causes variable attenuation of the laser beam. A speed of rotation and duty cycle of the at least one rotating disc can be regulated based on feedback from an attenuated aiming beam.

BRIEF DESCRIPTION OF THE FIGURES

These and other characteristics of the present invention will be more fully understood by reference to the following detailed description in conjunction with the attached drawings, in which.

DETAILED DESCRIPTION

Figure 1:
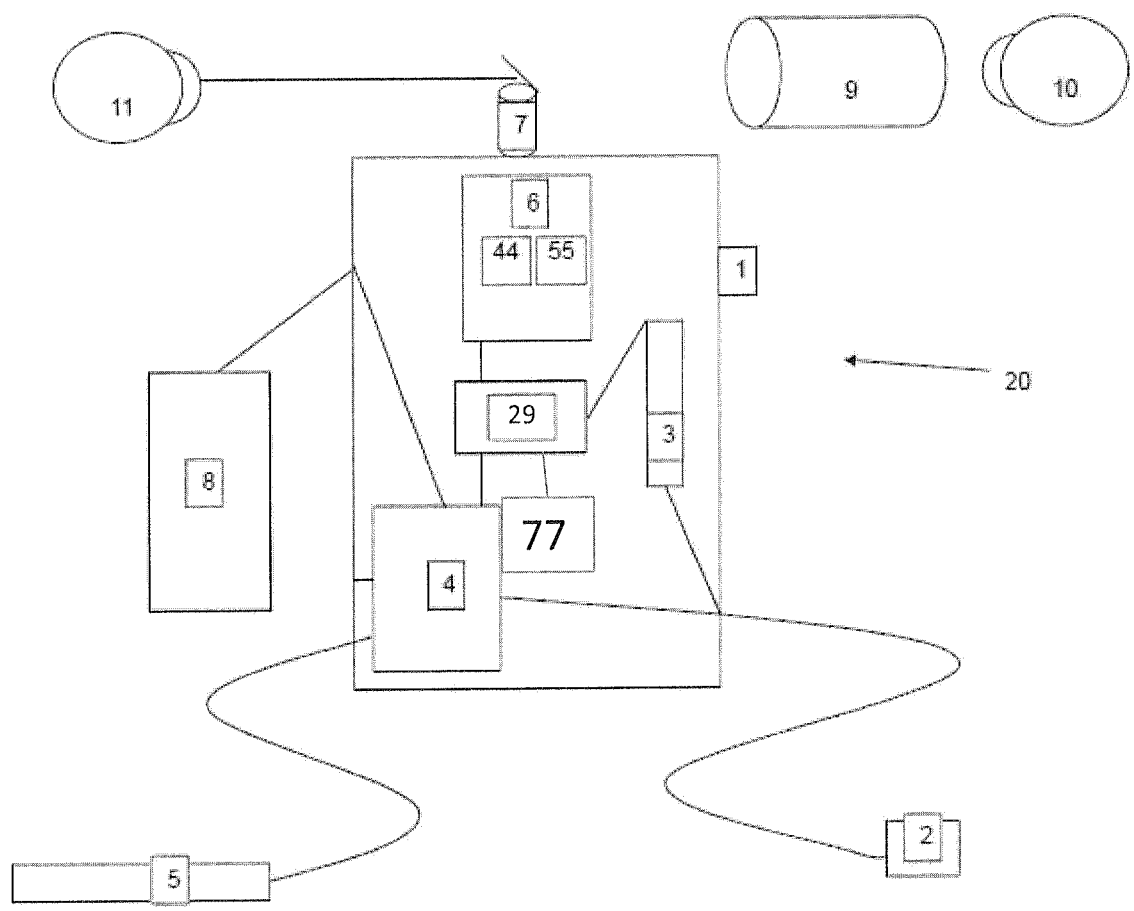
FIG. 1 is a schematic illustration of a compact surgical apparatus, in accordance with aspects of the present invention.

An illustrative embodiment of the present invention relates to laser systems, and their methods of use, that produce controllable, modulated, variable pulse width trains. In particular, the present invention relates to visible laser systems, and their methods of use, that produce modulated pulse trains of visible laser of the appropriate pulse length, duty cycle, and power to perform both thermal and non-thermal laser treatments.

An example embodiment of the present invention relates to provisioning a surgical laser apparatus that enables customizable laser power modulation for thermal and non-thermal laser treatments. The surgical laser apparatus utilizes a laser source in the form of a laser unit. The laser unit can be mounted to or integrated into ophthalmic optical equipment like a slit lamp, a surgical microscope, fundus camera or a handheld lens system. The laser unit can also have other delivery systems such as fiber optic coupled hand pieces, endo-laser probes, or scanners for pattern generation. Additionally, the laser unit can be utilized for a variety of non-ophthalmic medical indications including but not limited to dermatology, vascular surgery, and ear nose and throat surgery.

An example embodiment of the present invention relates to provisioning an apparatus to convert a continuous wave (CW) laser, produced by the surgical laser system, into a format to enable customizable laser power modulation for thermal and non-thermal laser treatments. The apparatus may be placed either between the CW laser system and its delivery device, such as slit lamp adapter, endolaser fiber or laser indirect ophthalmoscope, or at the aperture of its delivery device to modulate the laser beam. The apparatus serves as a beam modulator and allows the delivery of a modulated beam to the targeted tissues that can be mounted to or integrated into ophthalmic optical equipment like a slit lamp, a surgical microscope, fundus camera or a handheld lens system. The surgical laser system can also have other delivery systems such as fiber optic coupled hand pieces, endo-laser probes, or scanners for pattern generation. Additionally, the apparatus can be utilized for a variety of non-ophthalmic medical indications.

These and other features and advantages of the invention will become apparent from the description which follows, given by way of example, with reference to the accompanying schematic drawings.

FIGS. 1 through 17, wherein like parts are designated by like reference numerals throughout, illustrate an example embodiment or embodiments of a system that produces modulated pulse trains of visible laser of the appropriate pulse length, duty cycle, and power to perform both thermal and non-thermal laser treatments, according to the present invention. Although the present invention will be described with reference to the example embodiment or embodiments illustrated in the figures, it should be understood that many alternative forms can embody the present invention. One of skill in the art will additionally appreciate different ways to alter the parameters of the embodiment(s) disclosed, such as the size, shape, or type of elements or materials, in a manner still in keeping with the spirit and scope of the present invention.

Turning to FIGS. 1 through 4, a compact surgical apparatus 20 embodying the invention, and corresponding method of use, are provided. The compact surgical apparatus 20 includes a laser unit 1 and an operating optical system 9. The laser unit 1 includes a power regulator 3, a laser central processing unit (CPU) 4a laser source assembly 6 and.

In accordance with an example embodiment of the present invention, the laser source assembly 6 is a diode laser assembly configured to produce a controllable laser beam. The laser source assembly 6 includes a visible laser source 55 and aiming laser source 44. The visible laser source 55 and the aiming laser source 44 are diodes configured to provide an adjustable laser beam output. In particular, the visible laser source 55 and the aiming laser source 44 are configured to produce an aiming beam power setting (PI), a low level power setting (PII) that is greater than the aiming level power setting and causes generation of a continuous low-level laser (LLL) beam for warming target tissues without causing photocoagulation, and a high level power setting (PIII) that has an upper level power setting greater than the low level power setting and causes generation of a high level therapy controlled pulse width train laser beam, Additionally, the laser source assembly 6 is able to create a controllable laser beam at each of the various power settings (e.g., PI, PII, PIII), including creating pulse width trains alternating between the power settings. For example, the laser source assembly 6 can produce pulse width trains alternating between the LLL beam and the high level therapy bream.

In accordance with an example embodiment of the present invention, the visible laser source 55 emits laser in the visible spectrum such as in the violet range, nominally 405±20 nm, the blue range, nominally 445±20 nm, the green range, nominally 520±20 nm, or in the yellow range, nominally 570+20 nm, 610+20 nm or the red range, nominally 635±20 nm or 658±20 nm. Additionally, the visible laser source 55 is configured to create an alternating pulse laser beam. For example, the visible laser source can create a laser beam alternates between the LLL beam and the high level therapy beam. In contrast, the aiming laser source 44 is configured to emit a continuous visible laser beam of a different wavelength than that of the visible laser source 55 (at least 20 nm shorter or longer than the treatment laser wavelength) with the aiming laser source 44 beam being coaxial with the laser beam from the visible laser source 55. As would be appreciated by one skilled in the art, the different laser sources 44, 55 of the laser source assembly 6 and the various laser beam levels provided therefrom can be controlled based on the level of power or current provided to the laser source assembly 6.

In accordance with an example embodiment of the present invention, the laser source assembly 6 is constructed from at least one of a diode laser, a diode laser array, or a DPSS laser source. The DPSS laser source may have a gain medium such as Nd:YAG, Nd:YVO4, Nd:YLF, Ho:YAG, Er:YAG, Yb:YAG, and Yb:YVO4 that emits a laser that travels through a frequency converter that can be made of a variety of materials, including but not limited to, KTP, LBO, BBO, and the like to produces a laser in the visible spectrum such as 532 nm, 566 nm, 593.5 nm, 589 nm, 633-647 nm, 660 nm, and 690 nm. The wavelengths of 405±20 nm, 445±20 nm, 635±20 nm, 658±20 nm, 610+20 nm, 520±20 nm 532 nm, 566 nm, 593.5 nm, 589 nm, 633-647 nm, 660 nm, or 690 nm (produced by the laser source assembly 6) are suitable for the optics to focus and direct a treatment beam into a treatment area, an illuminator such as a slit lamp, and means for observing the treatment area. As would be appreciated by one skilled in the art, the laser source assembly 6 further includes housing, multiple optical elements such as lenses, beam expanders, beam combines, dichroic mirrors, photodiode and can further include a heat sink and means to attach it to the laser outlet.

Continuing with FIGS. 1-4, the laser unit 1 can be attachable to the operating optical system 9, such as for example, a slit lamp. This configuration enables the laser beam and the anterior focal point of the operating optical system 9 to be confocal. In other words, the laser beam produced by the laser unit 1 and the anterior focal point of the operating optical system 9 have the same foci. In accordance with an example embodiment of the present invention, the laser unit 1 can also be connected to a power source 2. The power source 2 provides the power to the compact surgical apparatus 20. As would be appreciated by one skilled in the art, the power source 2 can be a power supply box of the operating optical system 9, e.g. slit lamp, a battery, or a transformer providing the required power to drive the laser system, or other power source.

Additionally, the laser central processing unit CPU 4 is supplied with electric current from the power source 2 at a given voltage or voltage range. The electrical current levels can be adjusted to produce multiple (e.g., three) different power settings of a controllable laser beam produced by the laser source assembly 6. The laser CPU 4 can be activated by triggering a laser switch 5, such as a hand or foot switch trigger, which is communicatively attached to the laser CPU 4 via wired or wireless connection. When the laser CPU 4 is triggered through the laser switch 5, a predetermined adjustable pulse of relatively low current is supplied to a laser driver 29 included within or otherwise connected to the laser unit 1. The laser driver 29 uses the current from the power supply 2 through the power regulator 3 to provide relatively high current to the laser source assembly 6 to produce a pulse or train of pulses (pulse envelopes) of treatment laser beam of predetermined pulse characteristics. A "relatively high current" indicates that the current is substantially above the diode laser threshold level (note: The current for which the gain satisfies the lasing condition is the threshold current of the laser. Below the threshold current a very low level of light is emitted by the laser structure. When there is a current supplied to the laser that is larger than the threshold current, the output power of the laser increases linearly with the applied current). The specific current levels can vary, as would be appreciated by those of skill in the art. However, in accordance with the present invention the "relatively high current" is defined as being at least two times the value of the threshold current.

In accordance with an example embodiment of the present invention, the laser unit 1 is connected to and/or includes a signal generator 77 that can produce a regular wave form of variable voltage (e.g., 0-5 volts). The signal generator 77 is connected to the laser driver 29 to modulate the output electric current going to the diode to the same shape amplitude of the modulating waveform. The signal generator 77 converts the laser output from a laser source 55 to a modulated pulse or pulse trains. As would be appreciated by one skilled in the art, the different laser parameters such as the high laser power, low laser power, pulse train duration, frequency of laser pulsing within the pulse envelopes as well as other settings can be controlled by the user through a user control panel 8. The user control panel 8 can include any combination of hardware and software communicatively attached to the laser unit 1 and configured to provide control signals to the laser unit 1, and the components included therein (e.g., the signal generator 77).

In operation, for example, in accordance with one embodiment of the present invention, the laser unit 1 produces an aiming beam laser that originates from the laser source 44 and a treatment beam that originates from the visible laser source 55 with a laser output that alternates between three power level ranges namely high (PIII), low (PII) and OFF. High laser output (PIII) refers to a therapeutic range laser output that can provide photocoagulation at standard fluence and pulse duration settings, for example, at output power levels of 50 mW to 3000 mW. Low laser output (PII) refers to a laser output level that can be used for low level laser therapy that may gently warm and stimulate the tissues but is not sufficient to cause photocoagulation with the standard spot size (50 micron to 1000 microns) and pulse durations, for example, at output power levels of 1-49 mW. The low laser output power level can be either independently determined from the high laser output level by the user or be selected as a percentage of the high laser output level. Accordingly, as a user is aiming at the targeted tissues using the aiming beam, the visible laser source 55 receives no current from the laser driver 29 and the output is OFF. When the user fires the laser, the laser output out of the visible laser source 55 is delivered in the form of an envelope of trains of pulses with peak power (PIII) and trough power (PII) for a predetermined pulse envelope duration then the output goes back to OFF. The aiming laser source 44 outputs a continuous output at less than 1 mW (<1 mW) aiming power level independent from the different laser output laser levels from the visible laser source 55. Alternatively, the aiming laser source 44 may be switched off by the laser CPU 4 while the visible laser source 55 is producing laser output and switched on when the visible laser source 55 output is OFF.

The characteristic of the laser pulse(s) may depend on the pre-determined settings, as would be understood by those of ordinary skill in the art. One of ordinary skill in the art will additionally appreciate that it is the pulse current being significantly higher than the threshold current of the lasers being utilized that is relevant to the present invention. The specific current levels are merely illustrative of an example implementation. However, the relatively high current level utilized in the inventive system and method is an operationally significant contribution to the overall operability of the present invention, and as discussed herein, is generally twice the threshold current level, or more.

Figure 3:
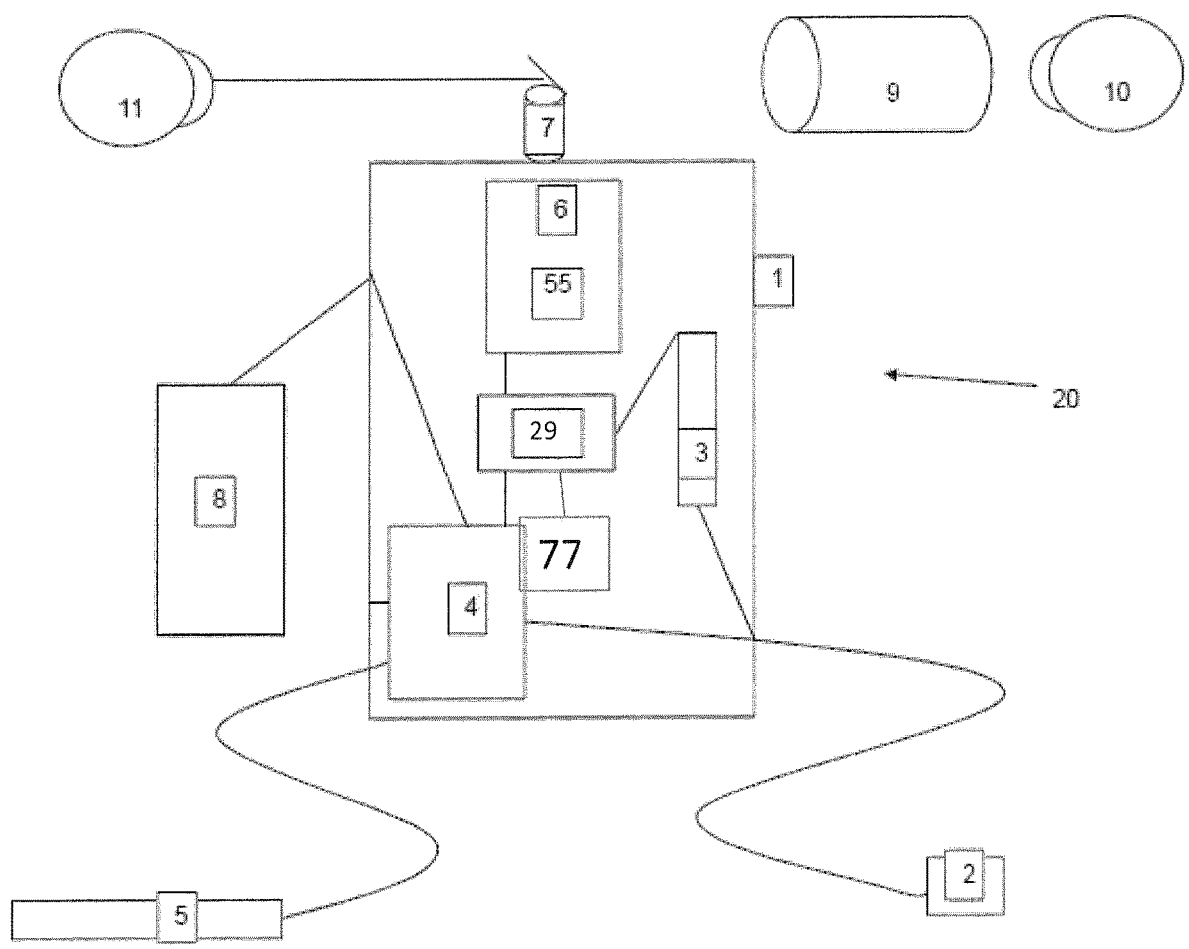
FIG. 3 is a schematic illustration of a compact surgical apparatus, in accordance with an example embodiment of the present invention.

As depicted in FIGS. 1 and 3, the laser beam emitted from the laser source assembly 6 passes through a laser outlet assembly 7. The laser outlet assembly 7 is configured to direct and control a size and focus of the laser beam provided by the laser source assembly 6. In accordance with an example embodiment of the present invention, the laser outlet assembly 7 includes one or more lenses, beam expanders, apertures, and/or prisms through which the laser energy passes. FIGS. 1 and 3 also depict an operator's eye 10 (e.g., the eye of the user of the compact surgical apparatus 20) and a treated eye 11 (e.g., the eye of the patient being treated with the compact surgical apparatus 20). In operation, the laser beam produced by the laser unit 1 passes through the laser outlet assembly 7 to the treated eye 11 to provide a modulated laser pulse train to the treated eye 11.

In accordance with an example embodiment of the present invention, the laser source assembly 6 includes a visible laser source 55 that emits laser in the visible spectrum such as in the violet range, nominally 405±20 nm, the blue range, nominally 445±20 nm, the green range, nominally 520±20 nm, or in the yellow range, nominally 570+20 nm, 610+20 nm or the red range, nominally 635±20 nm or 658±20 nm. The same laser diode module of the laser source assembly 6 that is capable of producing continuous low laser aiming beam and is capable of producing high power treatment beam. The laser source assembly 6 can be in the form of, for example, a diode laser, diode laser array, or a DPSS laser source. The DPSS visible laser source 55 may have a gain medium such as Nd:YAG, Nd:YVO4, Nd:YLF, Ho:YAG, Er:YAG, Yb:YAG, and Yb:YVO4 that emit a laser that travels through a frequency converter that can be made of a variety of materials, including but not limited to, KTP, LBO, BBO, and the like to produces a laser in the visible spectrum such as 532 nm, 566 nm, 593.5 nm, 589 nm, 633-647 nm, 660 nm, and 690 nm.

In accordance with an example embodiment of the present invention, both aiming and treatment beams can originate from the same visible laser source 55, as depicted in FIG. 3. In this configuration, the laser output from the visible laser source 55 alternates between three power level ranges namely high (PIII), low (PII), and aiming (PI). High laser output (PIII) refers to a therapeutic range laser output that can provide photocoagulation at standard fluence and pulse duration settings for example at output level of 50 mW to 3000 mW. Low laser output (PH) refers to a laser output level that is typically used for low level laser therapy that may gently warm and stimulate the tissues but is not sufficient to cause photocoagulation with the standard spot size and pulse durations for example 1-49 mW. In particular, the non-photocoagulative treatments heat the tissue, selectively activate some intracellular enzymes and processes and initiate some signal carrier cells, which initiate the therapeutic response. This healing response helps healing the disease being treated without irreversibly damaging (coagulating) any of the treated tissues. Hence, activating the healing response without coagulating tissue and thus losing vision is a better treatment method.

Figure 2:
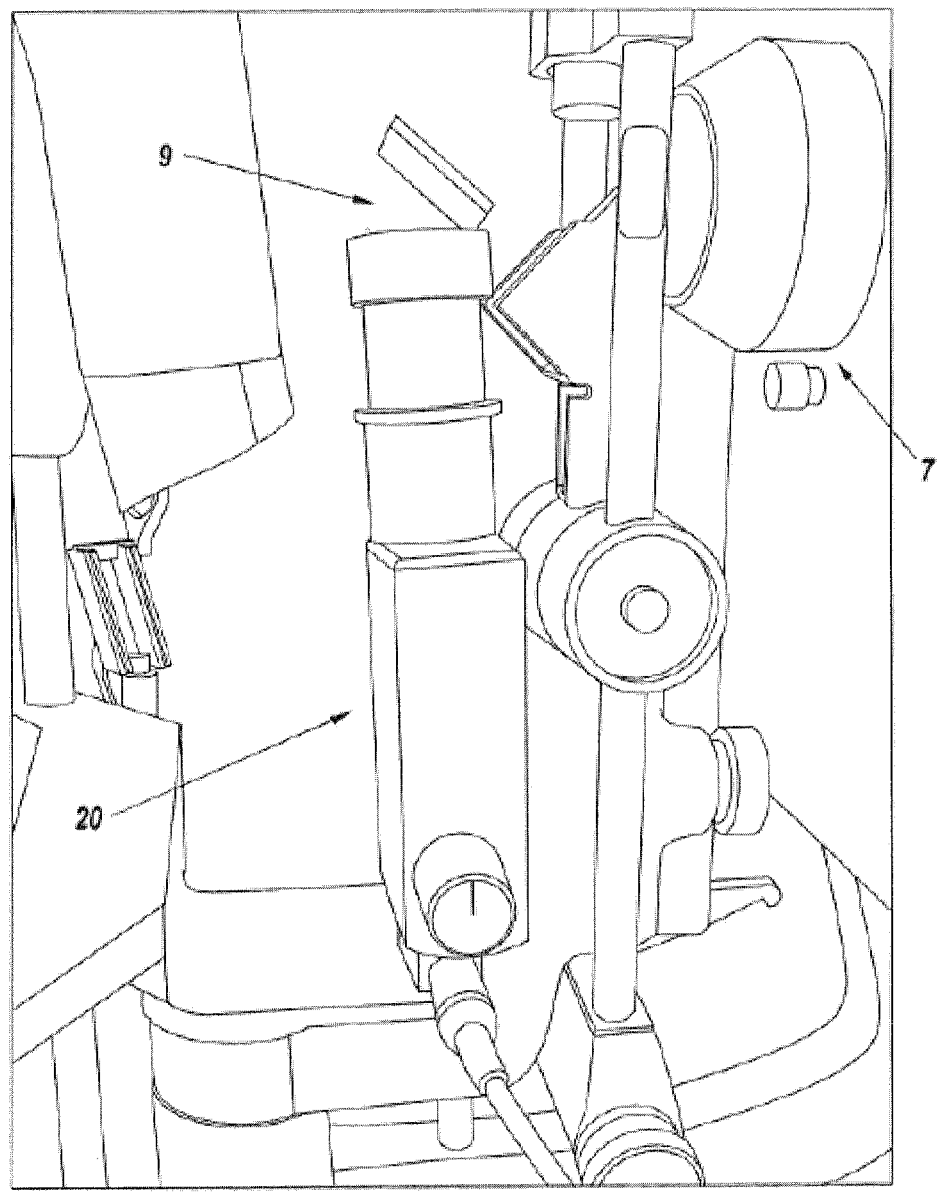
FIG. 2 is an image of a side view of a prototype compact surgical apparatus, in accordance with aspects of the present invention.

As would be appreciated by one skilled in the art, the low laser output power level can be either independently determined from the high laser output level by the user or be selected as a percentage of the high laser output level. The aiming (PI) laser can be substantially the same as the laser beam output by the aiming laser source 44, as discussed herein. In operation, as the user is aiming (e.g., through operator's eye 10) at the targeted tissues (e.g., treated eye 11) using the aiming beam, the visible laser source 55 is receiving very low current from the laser driver 29 and the output power is provided at an aiming level, which is typically less than 1 mW. When the user fires the laser, the laser output out of the visible laser source 55 is delivered in the form of a train of pulses with high peak power (PHI) and low trough power (PII) for a predetermined pulse envelope duration then the output goes back to aiming level (PI). For example, the laser output can include pulse width train laser beam in the range of 5 μsec to 100 μsec time duration between each pulse. The alternating train of pulses produces a high level therapy laser beam suitable for treating target tissues. Additionally, the high level power of the high level therapy controlled pulse width train laser beam is of sufficient power to cause photocoagulation of tissue, but the controllable laser beam output does not cause significant collateral photocoagulation damage to other tissues surrounding the target tissues FIGS. 1-3 depicts a detailed view of the compact surgical apparatus 20 and, in particular, the configuration of the operating optical system 9 and the laser outlet assembly 7. With respect to the additional components of FIGS. 1-3, the various conventional components described herein and their construction individually are well known to those skilled in the art and therefore will not be described in greater detail herein. In operation, the compact surgical apparatus 20, as depicted in FIGS. 1-3, allows the operator to modulate the delivered laser energy combining different proportions of low power (PII) and high power during the treatment periods. This allows a wide range of therapeutic effects such as photocoagulation, selective tissue targeting and tissue warming as well as low level thermotherapy and or combination thereof.

Figure 4:
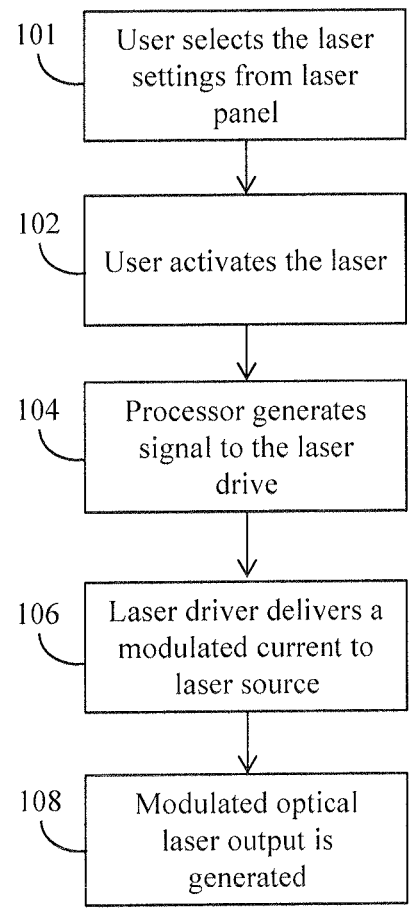
FIG. 4 is a flowchart illustrating a method of utilizing a surgical apparatus, in accordance with aspects of the present invention.

FIG. 4 depicts a brief description of the method of utilizing the compact surgical apparatus 20 discussed with respect to FIGS. 1-3, according to the present invention. The method of use begins (after any initial setup steps) with the provision of the laser pulse parameters by the user through the control panel 8 (step 101). The laser CPU 4 is initialized and provides current at a level sufficient to drive the diode laser source (44, 55) to emit a controllable continuous low energy visible laser beam that is used as the aiming beam based on the user provided parameters, as would be readily determinable by those of skill in the art with a given laser. The aiming beam either originates from the aiming laser source 44 or alternatively from the visible laser source 55, as discussed with respect to FIG. 3, and the user utilizes the aiming beam to locate and aim to the desired area for treatment on the treated eye 11. While aiming the laser beam, the user can make any necessary adjustments to the laser beam parameters at the laser outlet assembly 7 through control panel 8 (step 101) prior to activation of the treatment laser beam. As would be appreciated by one skilled in the art, the parameters can include adjusting the aiming beam power level, high power level, low power level, the pulse envelope duration, the laser pulse frequency, duty cycle and the same.

Figure 5:
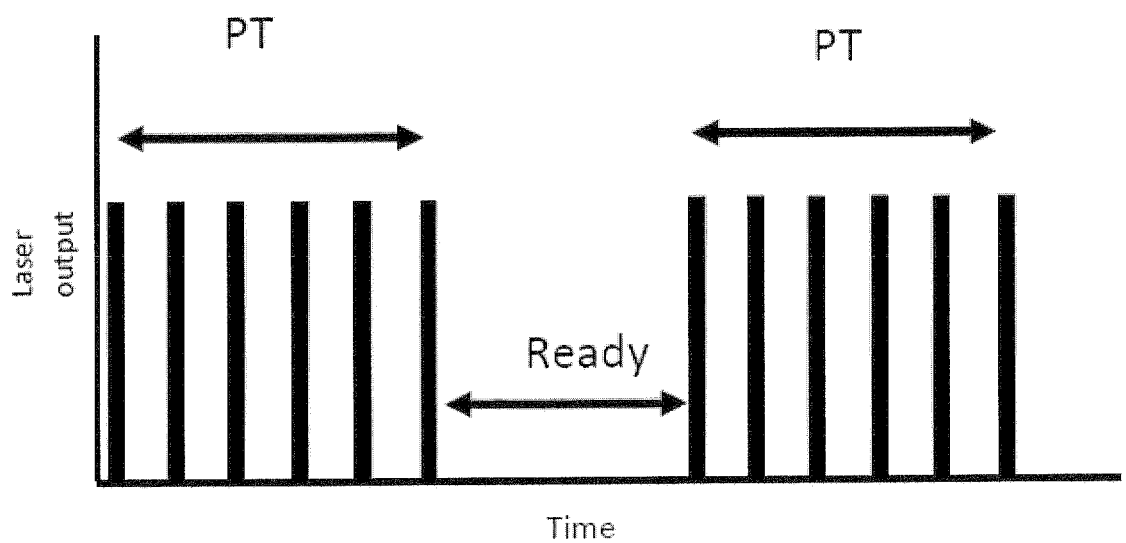
FIG. 5 is an illustration of a pulsed laser capable of producing trains of laser pulses, in accordance with aspects of the present invention.

When a treatment laser beam is desired, the user triggers the laser CPU 4 by activating the laser switch 5 (step 102). When the laser CPU 4 is triggered, the processor generates a signal, via the signal generator 77, to the laser drive 29 to supply a modulating relatively low current (step 104). In response, the laser driver 29 outputs a relatively higher current that is supplied to the laser source 55 of the laser source assembly 6 (step 106). A modulated laser pulse train is produced from the supplied current and a treatment laser beam emits in the direction of the treated eye 11 (step 108). The treatment laser beam is modulated and can continue for a predetermined period of time, as dictated by the operator configuration. Overall, the process depicted in FIG. 4 provides generation of an aiming laser beam, a low level power setting that is greater than the aiming level power setting, and causes generation of a continuous low-level laser (LLL) beam for warming target tissues without causing photocoagulation. The process also provides a high level power setting that has an upper level power setting greater than the low level power setting and causes generation of a high level therapy controlled pulse width train laser beam. As would be appreciated by one skilled in the art, the generating of the controllable laser beam output by the at least one laser diode source 44, 55 is designated by the three different power settings, such that the three different power settings are adjusted by adjusting electrical current levels at a given voltage FIG. 5 is an illustration of one embodiment of the modulated laser beam that the compact surgical apparatus 20 is capable of producing. In particular, FIG. 5 depicts trains of laser pulses with ultra-short pulses of 1.67 microseconds-10,000 microseconds with off period of 31.67-190,000 microseconds. When the laser is activated, it fires an envelope of pulses (PT). At the conclusion of the train of pulses, the treatment laser beam is off (Ready State) until it is triggered again by the user. FIG. 5 depicts a pulsed laser beam between a high level power output (PiII) and no output during the envelope of pulses (PT) and the laser beam being OFF during a Ready period.

In accordance with an example embodiment of the present invention, the train of pulses, as depicted in FIG. 5, has a thermal relaxation time less than a thermal relaxation time of the targeted tissues. For example, the train of pulses can have a pulse width that is less than 10 milliseconds or the train of pulses can have pulses greater than 1.67 microseconds. The train of pulses is optimized to confine the thermal effect to the pigmented cells, such as retinal pigment epithelium (RPE), without affecting the surrounding non pigmented tissues such as the neurosensory retina of the eye (e.g., treated eye 11). As would be appreciated by one skilled in the art, to achieve thermal confinement without significant build-up of tissue heating, laser energy should be delivered in pulses shorter than the time constant of the absorbing tissue. In case of retinal treatments (e.g., to treated eye 11), the RPE time constant is 1 to 30 microseconds. The loss of tissue function associated with the traditional photocoagulator (PC) treatments is nullified due to the lower energies used and thus not coagulating the retina photoreceptors in the surrounding transparent layers.

In accordance with an example embodiment, the pulsed laser output has a wavelength in the visible range suitable for a visible diode laser. The pulsed laser output can have a pulse on time of 1.67 microseconds to 10,000 microseconds, a pulse off time of 31.67 microseconds to 100,000 microseconds, and the like.

In accordance with an example embodiment of the present invention, the high level power output time of the compact surgical apparatus 20 is less than 1 to 10 milliseconds. In accordance with one embodiment of the present invention, laser pulses of 1.67 microseconds up to 10,000 microseconds are provided by the compact surgical apparatus 20 with high power levels of up to 3 Watts. By way of illustration, and without limitation, pulse trains of up to 500 of these pulses with a variable duty cycles from 5% to 100% are provided. FIG. 5 depicts that the laser power is off in between the laser high output power pulses.

Figure 6:
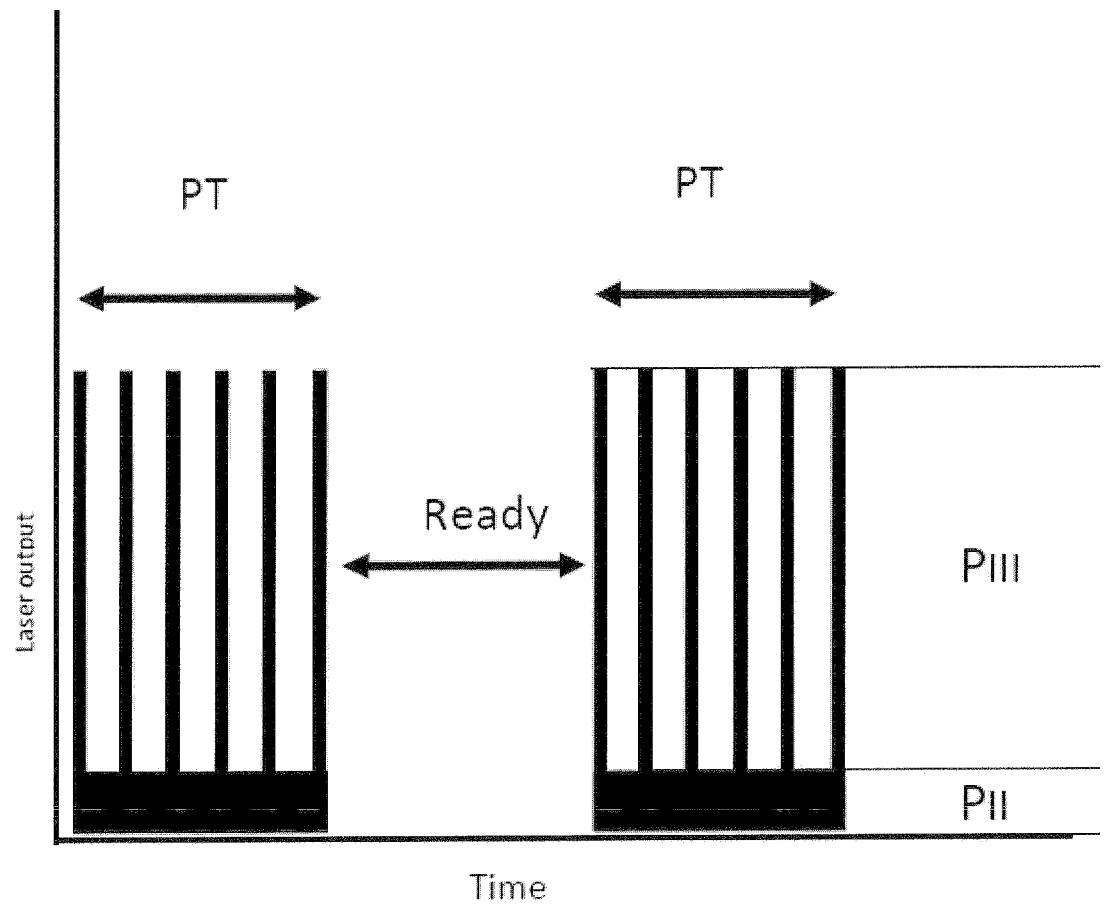
FIG. 6 is an illustration of an output of a visible laser, in accordance with aspects of the present invention.

FIG. 6 is an illustrative embodiment of a treatment laser pulsed output produced by the compact surgical apparatus 20 with a train of pulses envelopes. In particular, FIG. 6 depicts a train of pulses in which each envelope consists of a high power laser output alternating with a low power output. The compact surgical apparatus 20 is capable of producing trains of laser pulses with trains of pulses with ultra-short high power (PIII) pulses of 1.67 microseconds-10,000 microseconds with low power (PII) period of 31.67-190,000 microseconds. When the laser is activated, it fires an envelope of pulses (PT). At the conclusion of the train of pulses, the treatment laser beam is off (Ready State) until it is triggered again by the user.

In accordance with an example embodiment of the present invention, the high level power output time of the compact surgical apparatus 20 is 1 millisecond to 10 milliseconds. The micro pulses of high laser power of 1.67 up to 10,000 microseconds are provided by the compact surgical apparatus 20 with high power levels (PHI) of 50 W up to 3 W, alternating with low level laser output (PII) levels, so that the laser irradiation of the tissues is continuous during the total time of the pulse train. By way of illustration, and without limitation, continuous tissue irradiation with low power laser with trains of up to 30000 laser power spikes of these pulses with a variable duty cycles from 5% to 100% are provided. In this example embodiment of the present invention, the laser power is not OFF but rather at low level laser exposure (PII) between the laser high output power pulses, as depicted in FIG. 6. This approach allows longer tissues laser exposure time, as well as, gentle tissue warming and stimulation between the high laser power pulses, without significantly increasing the total laser energy level delivered or cumulative tissue heating. This approach allows selective tissue targeting without coagulative damage.

In an example embodiment of the present invention, the compact surgical apparatus 20 produces the pulsed laser output with a train of pulses that have high output times optimized for confinement of thermal effects to sites adjacent to the treated eye 11. A plurality of pulses is directed to the same target site treated eye 11. A temperature rise at the target site treated eye 11 is non-additive from pulse to pulse. By way of illustration, and without limitation, the target site treated eye 11 can have an area of about 50 microns to 3 mm. In this method of treatment, the pulsed output has a wavelength range in the visible, and the pulsed output can have a wavelength range of 400 nm to 690 nm.

Figure 7:
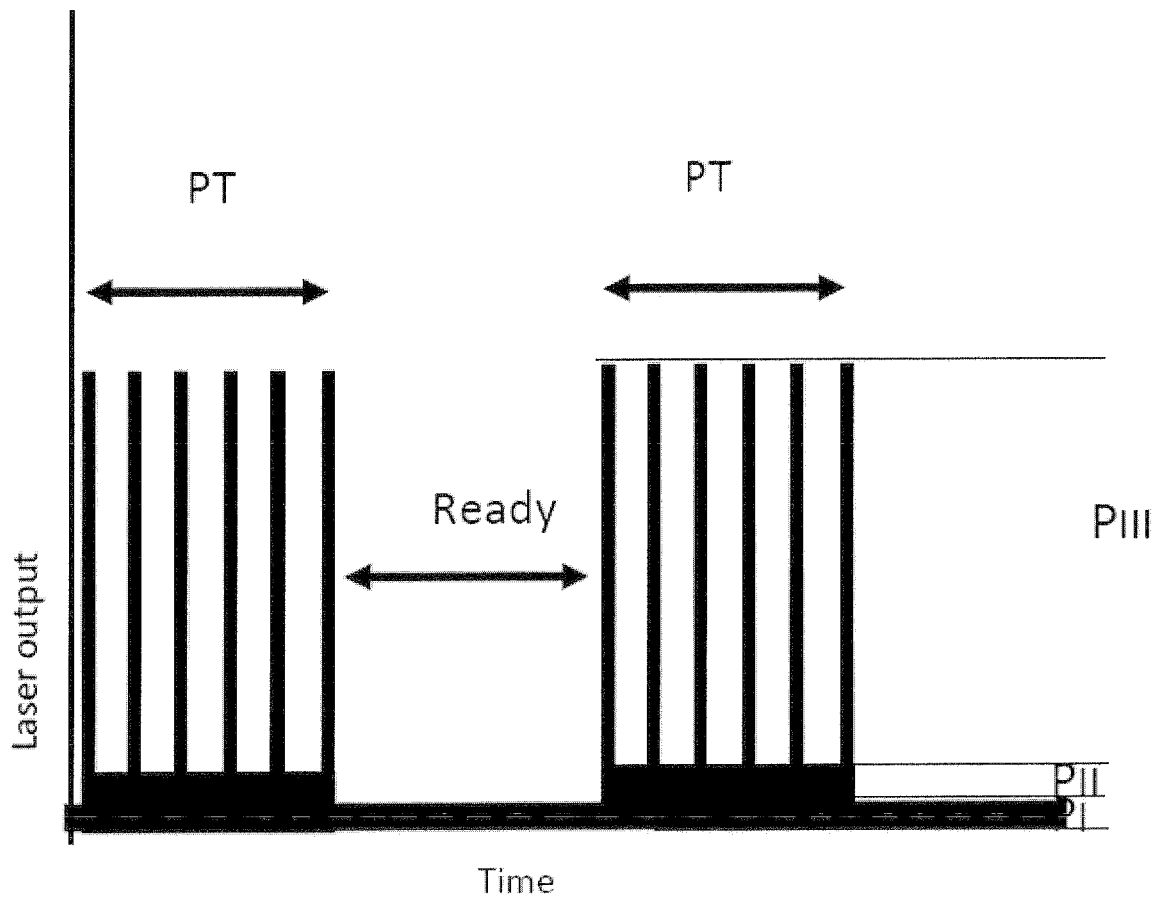
FIG. 7 is an illustration of an output of a visible laser, in accordance with aspects of the present invention.

FIG. 7 is an illustrative embodiment of a treatment laser pulsed output of the compact surgical apparatus 20 with a train of pulses envelopes, where each envelope consists of high power laser output alternating with low power output. The compact surgical apparatus 20 is capable of producing trains of laser pulses with trains of pulses with ultra-short high power (PIII) pulses of 1.67 microseconds-10,000 microseconds with low power (PII) period of 31.67-190,000 microseconds. In this example embodiment of the present invention, the visible laser source 55 produces both the aiming and treatment laser beams (as depicted in FIG. 3). When the laser is activated (e.g., via the laser switch 5), the compact surgical apparatus 20 fires an envelope of pulses (PT) alternating between high (PIII) and low (PII) during the envelope. At the conclusion of the train of pulses, the treatment laser beam reverts back to the aiming beam level power (PI) until the envelope of pulses is triggered again by the user.

Figure 8:
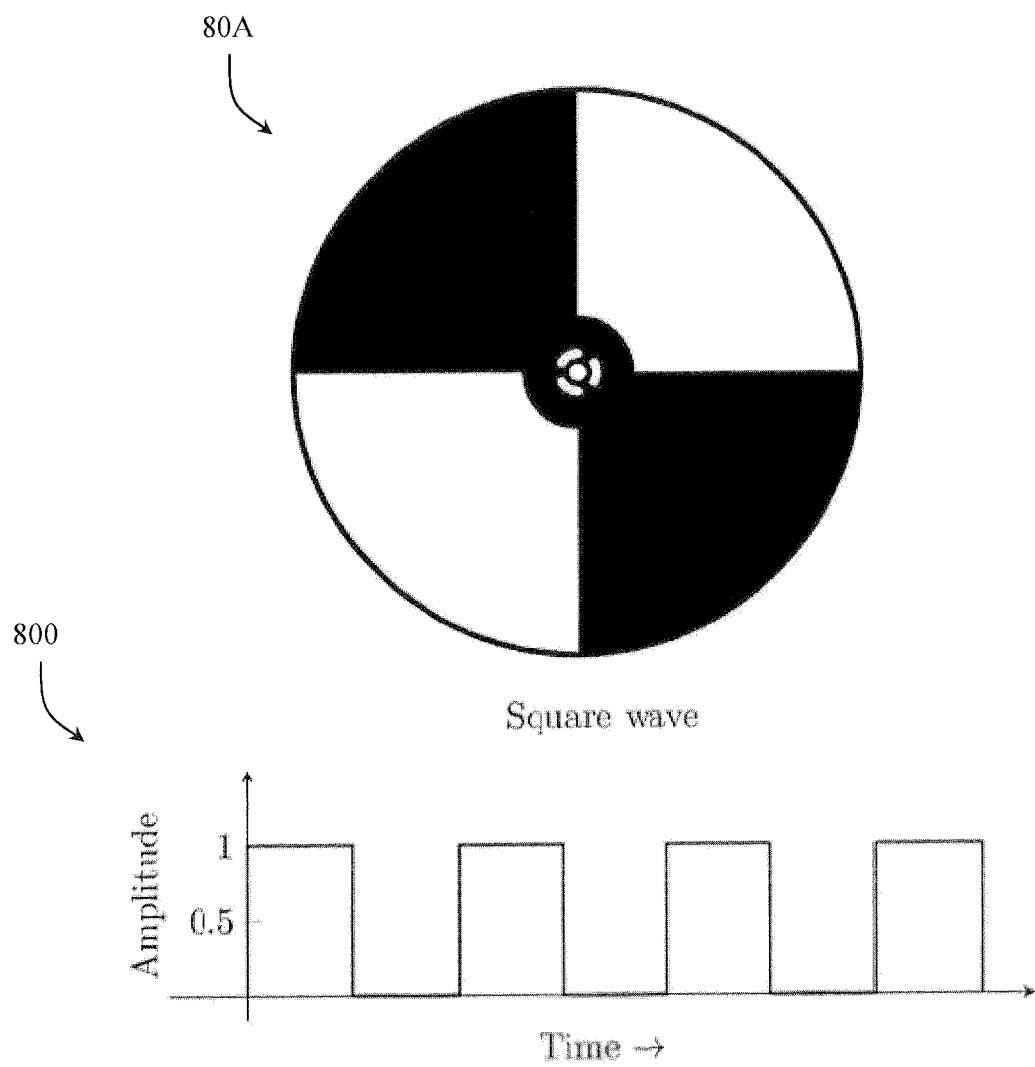
FIG. 8 is a front view of chopper discs of the prior art and the waveform of a continuous wave (CW) laser after passing through the optical chopper discs.

FIG. 8 depicts a rotating disc 80A for utilization with an optical chopper 90 in accordance with an example embodiment of the present invention. Specifically, FIG. 8 depicts the rotating disc 80A that is utilized to control an envelope of pulses of laser beams provided by the compact surgical apparatus 20. The rotating disc 80A includes at least one barrier and at least one aperture. The rotating disc 80 laser is positioned perpendicular to the laser driver 29 such that the rotating disc 80A provides modulation to the laser beam. In particular, when a laser beam is perpendicular on the surface of the rotating disc 80A of an optical chopper 90, the at least one barrier interrupts the laser beam while the at least one aperture allows the laser beam to pass through the rotating disc 80A uninterrupted to output a high level therapy controlled pulse width train laser beam.

The controlled pulse width train laser beam output created by the rotating disc 80A results in a pulsed envelope laser beam. For example, the pulsed laser beam resulting from the rotating disc 80A is a laser beam chopped into a square wave beam 800. In particular, the rotating disc 80A in FIG. 8 chops a laser beam into a square wave form 800 with a peak of 100% power and troughs of 0% with a duty cycle of 50%. The duty cycle relies on the percentage of the angle of rotation in degrees corresponding to the "pass" part of the disc to the 360 degrees. In this example the duty cycle is (90+90)/360=50%. The variable duty cycle is determined and controlled by displacement of the rotating disc 80A relative to a path of the laser beam. As would be appreciated by one skilled in the art, the controlled pulse width train laser beam is controlled by a speed of rotation and distance from a center of rotation of the rotating disc 80A to mechanically chop the laser beam, such that to change the duty cycle of this square wave 800, the rotating disc 80A must be physically changed.

Figure 9:
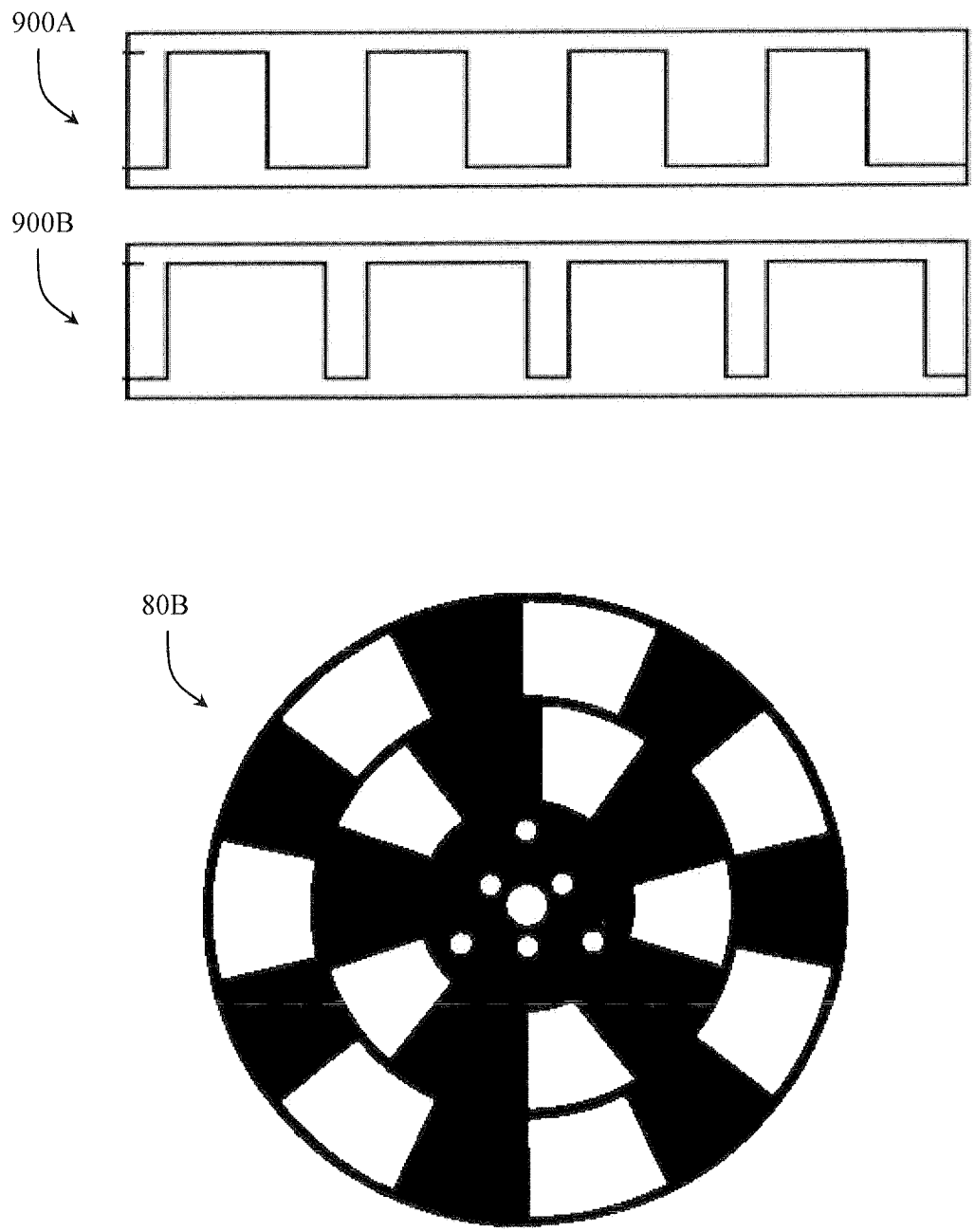
FIG. 9 is a front view of chopper discs of the prior art with two concentric rings of two different frequencies and duty cycles and the waveform of a CW laser after passing through its inner ring compared to outer ring.

Some more complicated rotating discs 80B, such as the one demonstrated in FIG. 9, can be utilized with the optical chopper 90. In particular, FIG. 9 depicts a rotating disc 80B that enables the flexibility to produce more than one duty cycle by passing the laser beam through different parts of the rotating disc 80B. This configuration allows a laser output of two or three duty cycles but not the continuous adjustment of the duty cycle. For example, waves 900A and 900B are the result of a laser beam passing through the outer and inner portions of the rotating disc 80B respectively.

Figure 10:
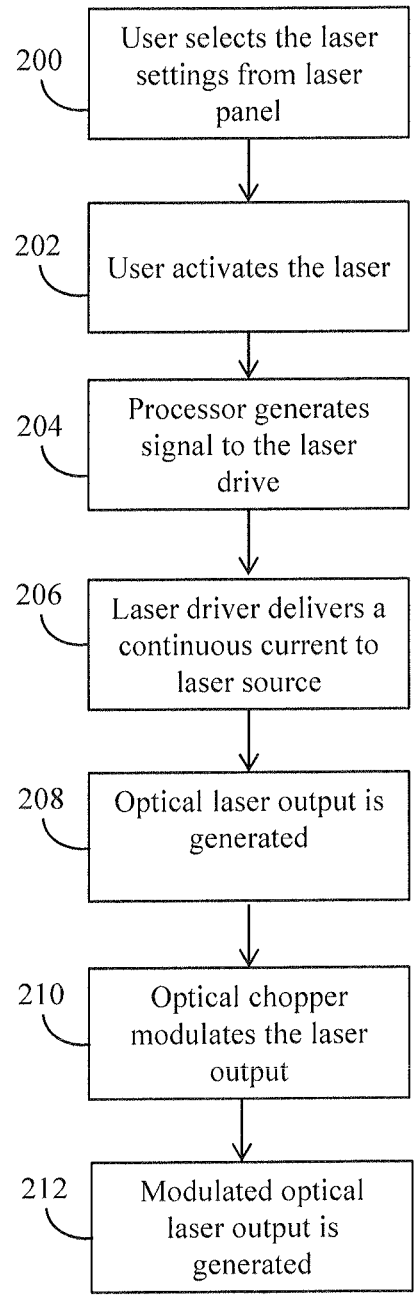
FIG. 10 is a flowchart illustrating a method of utilizing a surgical apparatus, according to one embodiment of the present invention, in accordance with aspects of the present invention.
Figure 11:
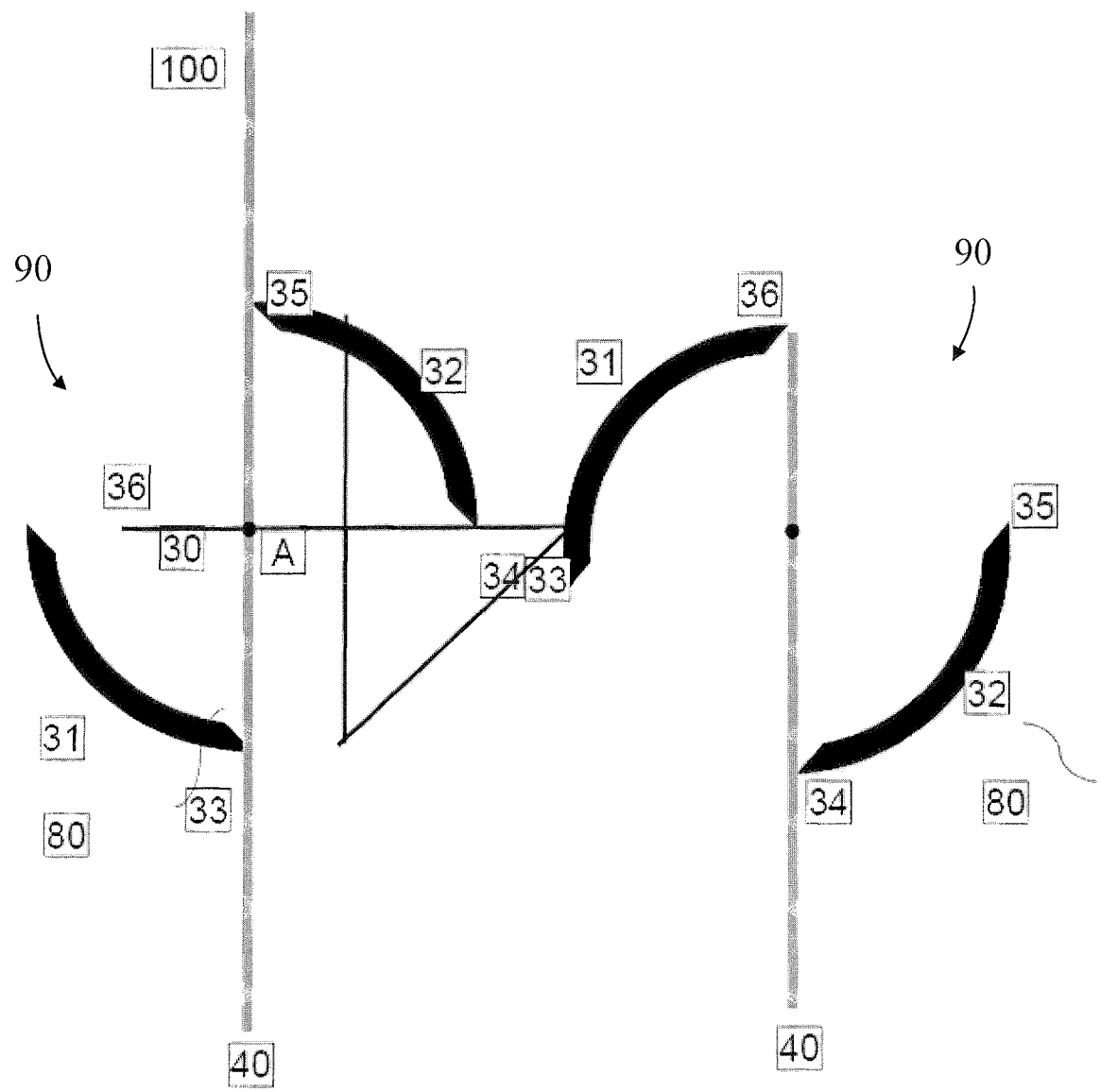
FIGS. 11A and 11B are cross-sectional views of an optical chopper disc rotating to chop a laser beam going through its center of rotation, in accordance with aspects of the present invention.
Figure 12:
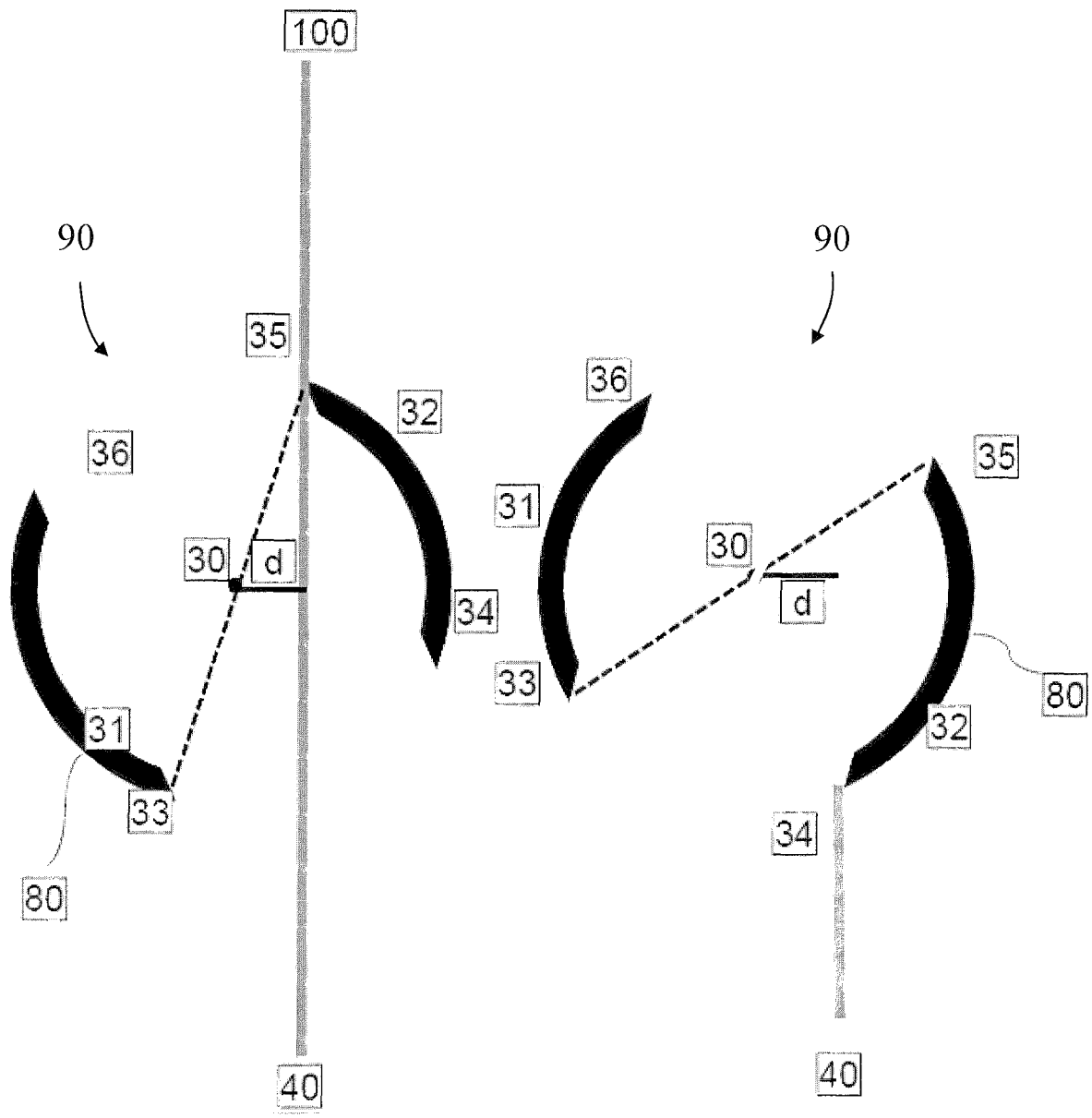
FIGS. 12A and 12B are cross-sectional views of an optical chopper disc while rotating to chop a laser beam passing at some distance from its center of rotation, in accordance with aspects of the present invention.

FIG. 10 depicts a method of utilizing the compact surgical apparatus 20 with an optical chopper 90 and rotating discs 80, 80A, 80B (as depicted in FIGS. 8-17) according to aspects of the present invention. The method of use begins (after any initial setup steps) with the provision of the laser pulse parameters by the user through the control panel 8 (step 200). In particular, the settings input into the control panel 8 dictate the optical chopper 90 speed and the relative relationship between the collimated laser beam 40 (as depicted in FIGS. 11A-14, 16, and 17) from the visible laser source 55 to the center of rotation of the optical chopper 90 rotating disc 80. Similarly, the laser CPU 4 provides current at a level sufficient to drive the laser source 44, 55 to emit a continuous low energy visible laser beam that is used as the aiming beam, as would be readily determinable by one of skill in the art for a given laser. The aiming beam either originates from the aiming laser source 44 or alternatively from the visible laser source 55. The user utilizes the aiming beam to locate and aim to the desired area for treatment on the treated eye 11, making any necessary adjustments to the parameters for the laser beam at the laser outlet assembly 7. Such adjustments to the parameters include but are not limited to the aiming beam power level, high power level value, low power level value, the pulse envelope duration, the laser pulse frequency, duty cycle, etc.

When a treatment laser beam is desired, the user triggers the laser CPU 4 by activating the laser switch 5 (step 202). When the laser CPU 4 is triggered by activation of the laser switch 5, the laser CPU 4 supplies modulating relatively low current (for example, enough to produce 1.1 to 49 mW of laser optical power) to the laser driver 29 (step 204). As a result, the laser driver 29 outputs of a relatively higher current (for example, enough to produce at least 50 mW or more of laser optical power) to the visible laser source 55 of the laser source assembly 6 (step 206) causing a CW laser pulse train being emitted in the direction of the treated eye 11, producing a CW treatment laser beam (step 208). The collimated laser beam 40 passes through the optical chopper 90 (step 210). The speed of rotation of the optical chopper 90 and the position of the collimated laser beam 40 in relation to the rotation center of the optical chopper 90 are determined by settings provided by the user in step 200. The optical chopper 90 in turn chops the collimated laser beam 40 into modulated laser beam 100 (step 212).

FIGS. 11A and 11B illustrate an example implementation of utilizing a compact surgical apparatus 20 with an optical chopper 90, according to one embodiment of the present invention. In this example embodiment of the present invention, the collimated laser beam 40 from the visible laser source 55 passes through the optical chopper 90. The optical chopper 90 includes the rotating disc 80 with alternating apertures and barriers and the optical chopper 90 provides the means for rotation of the rotating disc 80. For example, the optical chopper 90 can include a motor that rotates the rotating disc 80, controllers for controlling the rate of the rotating, and a power supply to power the optical chopper 90. In accordance with an example embodiment, the optical chopper 90 can shift the rotating disc 80 in a direction perpendicular to the longitudinal (or travel direction) axis of the collimated laser beam 40 while monitoring the collimated laser beam 40 input into the optical chopper 90 and modulated laser beam 100 output of from the optical chopper 90.

FIG. 11A shows the position of the rotating disc 80 of the optical chopper 90 at one point in time. A collimated laser beam 40 passes through the first aperture between points 33 and 34 of the rotating disc 80 (the aperture closer to the laser source) to pass through the center point of rotation 30 of the rotating disc 80 then exits un-interrupted through the opposite (second) aperture between points 35 and 36 of the rotating disc 80. FIG. 11B shows the position of the rotating disc 80 of the optical chopper 90 after rotating 90 degrees clockwise around the center point of rotation 30. At this point, the collimated laser beam 40 is blocked simultaneously by points 34 of the barrier part 32 and point 36 of barrier part 31 of the rotating disc 80. Similarly, for the next 90 degrees of clockwise rotation of the disc, the collimated laser beam 40 will be blocked by the barrier part 32. At the next 90 degree clockwise rotation of the rotating disc 80, the collimated laser beam 40 will go through the aperture between point 35 and 36, through the center point of rotation 30 before passing through the other aperture between points 33 and 34. At the next 90 degrees of clockwise rotation of the rotating disc 80, the collimated laser beam 40 will be blocked by the barrier part 3. The next 90 degree rotation will continue back to the point depicted in FIG. 11A, and so on. In this example, the optical chopper 90 converts the collimated laser beam 40 to a modulated laser beam 100. As the laser beam goes through the center point of rotation 30, the rotating disc 80 is bisected by the collimated laser beam 40 into two symmetrical halves and the collimated laser beam 40 will be chopped at a duty cycle of 50% and frequency depending on the rotation speed of the rotating disc 80.

For example, the duty cycle while the collimated laser beam 40 passes through the center point of rotation 30 depends on an angle A (angle 33, 30, 34) corresponding to the width of the aperture (33, 34). In particular, the duty cycle is determined by the following equation:

Duty cycle=Angle $A$/(Angle $A$+Angle $B$)

Whereas, Angle A is dependent on the aperture width and the radius of the rotating disc 80 as follows:

Angle $A$=2×ArcSin(Aperture width/(disc radius×2))

While Angle B is determined by the barrier width and the radius of the rotating disc 80 as follows:

Angle $B$=2×ArcSin(Barrier width/(disc radius×2))

On the other hand, the frequency of the laser modulation is determined by the speed of rotation of the rotating disc 80, as well as the number of apertures, as follows:

Pulse frequency (Hz)=speed of disc rotations per second×(number of disc apertures/2).

Figure 13:
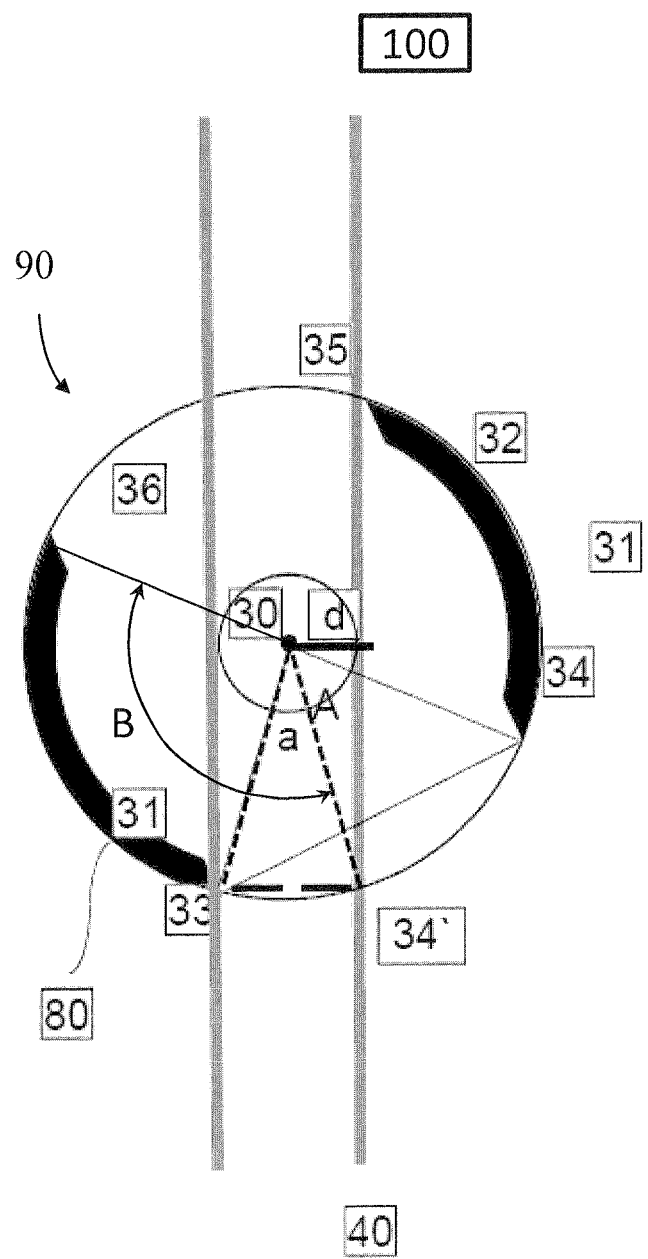
FIG. 13 is a cross-sectional view of an optical chopper disc where the rotating disc has multiple windows while rotating to chop a laser beam going through its center of rotation, in accordance with aspects of the present invention.

FIGS. 12A, 12B, and 13 show another example implementation of a collimated laser beam 40 being displaced by an optical chopper 90. In particular, FIGS. 12A, 12B, and 13 depict the collimated laser beam 40, provided from the visible laser source 55, passing through the optical chopper 90 and being displaced either by shifting the beam itself or moving the optical chopper 90 rotating disc 80. The collimated laser beam 40 is displaced laterally from the center point of rotation 30 by a distance (d). FIG. 12A shows the position of the rotating disc 80 of the optical chopper 90 at one point of time. As depicted in FIG. 12A, the collimated laser beam 40 passes through the first aperture between point 33 and 34 of the rotating disc 80 (the aperture closer to the laser source) to pass off the center point of rotation 30 of the rotating disc 80 by a horizontal distance (d) then exit un-interrupted through the opposite (second) aperture between points 35 and 36 of the rotating disc 80.

Similarly, FIG. 12B shows the position of the rotating disc 80 of the optical chopper 90 after rotating less than 90 degrees clockwise around the center point of rotation 30. At this position, the collimated laser beam 40 is blocked only by point 34 of the barrier part 32 of the rotating disc 80. As the rotating disc 80 rotates another 90 degrees in a clockwise direction, the collimated laser beam 40 will continue to be blocked by the barrier part 32. As the rotating disc 80 rotates past the barrier part 32 in a clockwise direction, the collimated laser beam 40 will go through the aperture between point 35 and 36, passing at a horizontal distance (d) from the center point of rotation 30 before being blocked by outer side of the barrier part 32 of rotating disc 80 at point 35. The rotating disc 80 continues to rotate in a clockwise direction before the collimated laser beam 40 can pass through both apertures and so on.

In this example, the optical chopper 90 converts the collimated laser beam 40 to a modulated laser beam 100. As the laser beam goes off the center point of rotation 30, the rotating disc 80 is bisected by the collimated laser beam 40 into two asymmetrical halves and the collimated laser beam 40 will be chopped at a duty cycle of less than 50% and frequency depending on the rotation speed of the rotating disc 80. As would be appreciated by one skilled in the art, the duty cycle relies on the horizontal distance of displacement (d) between the collimated laser beam 40 and center point of rotation 30. As a rule, the more the beam de-centration, the smaller the resulting duty cycle. This inverse relationship allows continuously variable duty cycles. For example, when the rotating disc 80 shifts to allow the collimated laser beam 40 to pass away from its center of rotation 30 by distance d, the new effective aperture width will be 33-34' as illustrated in FIG. 13.

In accordance with an illustrative example implementation, the duty cycle while the collimated laser beam 40 passes through the center point of rotation 30 depends on an angle A (angle 33, 30, 34') corresponding to the width of the aperture (33, 34'). In particular, the duty cycle is determined by the following equation:

Duty cycle=(Angle $A$−Angle $a$)/(Angle $A$+Angle $B$)

Whereas, Angle A is dependent on the aperture width and the radius of the rotating disc 80 as follows:

Angle $A$=2×ArcSin(Aperture width/(disc radius×2))

Angle $A$=2×ArcSin(chord width "33-34'"/(disc radius×2))

Angle $A$=2×ArcSin(2×displacement "$d$"/(disc radius×2))

While Angle B is determined by the barrier width and the radius of the rotating disc 80 as follows:

Angle $B$=2×ArcSin(Barrier width/(disc radius×2))

One the other hand, the frequency of laser modulation is determined by the speed of rotation of the rotating disc 80, as well as the number of apertures, as follows:

Pulse frequency (Hz)=speed of disc rotations per second× (number of disc apertures/2).

In accordance with an example embodiment of the present invention, the user determines the duty cycle through the control panel 8. In particular, the user utilizes the control panel 8 to modify the parameters that control the relative position of the collimated laser beam 40 relative to the center point of rotation 30 of the rotating disc 80. The parameters provided by the user in the control panel 8 are transmitted to and implemented via the laser CPU 4 using manual mechanical means, servo motors, actuators, prisms, mirror pairs or other means of displacing a laser beam. Alternatively, the relative position of the collimated laser beam 40 to the center point of rotation 30 of the rotating disc 80 can be changed using manual mechanical means (e.g., a mechanical crank).

Figure 14:
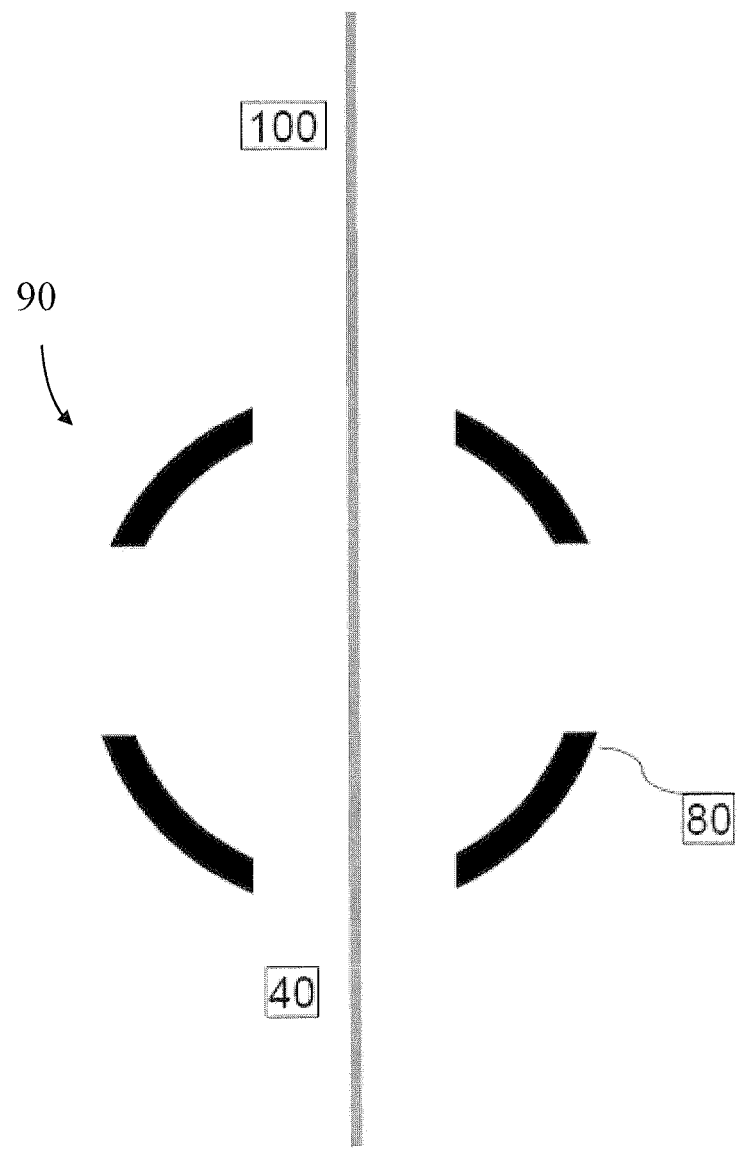
FIG. 14 illustrates the optical density of the barrier parts of the optical chopper disc according to three different example embodiments, in accordance with aspects of the present invention.

FIG. 14 shows an alternative embodiment of the optical chopper 90 where the rotating disc 80 of the optical chopper 90 has multiple apertures on each half of the rotating disc 80. For example, the optical chopper 90 can have two apertures on each half of the rotating disc 80 as depicted in FIG. 14. As would be appreciated by one skilled in the art, the optical chopper 90 can contain four, six, or eight apertures per half (even numbers). The configuration of the rotating disc 80 with multiple apertures within each half of the rotating disc 80 allows higher pulse frequencies to be produced. For example, a rotating disc 80 with two apertures on each half allows twice as much max laser chopping frequency than a rotating disc 80 with one aperture on each side at operating at the same spinning speed.

Similarly, when the collimated laser beam 40 passes through the center point of rotation 30:

Duty cycle=Angle $A$/(Angle $A$+Angle $B$)

Whereas, Angle A is dependent on the aperture width and the radius of the rotating disc 80 as follows:

Angle $A$=2×ArcSin(Aperture width/(disc radius×2))

While Angle B is determined by the barrier width and the radius of the rotating disc 80 as follows:

Angle $B$=2×ArcSin(Barrier width/(disc radius×2))

On the other hand, the frequency of laser modulation is determined by the speed of rotation of the rotating disc 80, as well as the number of apertures, as follows:

Pulse frequency(Hz)=speed of disc rotations per second×(number of disc apertures/2).

If the collimated laser beam 40 passes off the center point of rotation 30 by a distance d:

Duty cycle=(Angle $A$−Angle $a$)/(Angle $A$+Angle $B$)

Whereas, Angie A is dependent on the aperture width and the radius of the rotating disc 80 as follows:

Angle $A$2×ArcSin(Aperture width/(disc radius×2))

Angle $A$=2×ArcSin(chord width "33-34'"/(disc radius×2))

Angle $A$=2×ArcSin(2×displacement "$d$"/(disc radius×2))

While Angle B is determined by the barrier width and the radius of the rotating disc 80 as follows:

Angle $B$=2×ArcSin(Barrier width/(disc radius×2))

On the other hand, the frequency of laser modulation is determined by the speed of rotation of the rotating disc 80, as well as the number of apertures, as follows:

Pulse frequency (Hz)=speed of disc rotations per second× (number of disc apertures/2).

Figure 15A:
FIGS. 15A, 15B, and 15C illustrate three different barrier densities of the barriers of a chopping disc, in accordance with aspects of the invention.
Figure 15B:
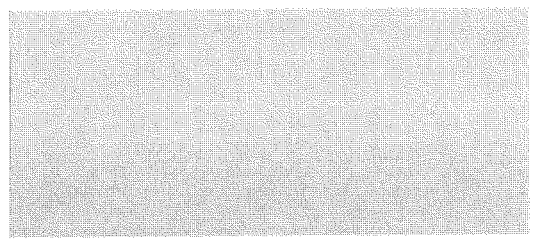
Figure 15C:
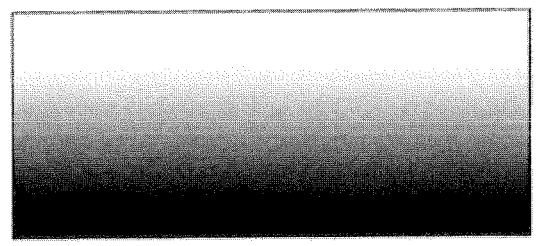

FIGS. 15A through 15C show three different barrier densities of the barrier parts 31, 32 of rotating disc 80 of the optical chopper 90. In particular, FIGS. 15A-15C depict attenuation barriers of variable size in such a way that displacement of the laser beam vertically relative to the at least one rotating disc causes variable attenuation of the laser beam. FIG. 15A shows a barrier that completely blocks the treatment wavelength (e.g., collimated laser beam 40) so that when the rotating disc 80 rotates the modulated laser beam 100 will have peaks of PIII power when the laser beam goes through the apertures and is OFF when blocked by the barriers.

Alternatively, FIG. 15B shows a partial blocker barrier part 31, 32. The partial barrier allows the collimated laser beam 40 to be chopped into peaks of PIII power when passing through the apertures and alternating with low PII power when passing through the partially blocking barrier. In other words, the barrier partially blocks the laser beam so that the laser beam peaks at a high therapy power level when the laser beam passes through the at least one rotating disc uninterrupted and alternates to a low-level laser therapy power level when the at least one barrier partially interrupts the laser beam. FIG. 15C shows another embodiment where the barrier part 31, 32 is a variable optical density filter. The optical chopper 90 will chop the beam the same way as in FIG. 15B, however, the degree of attenuation of the beam can be adjusted by adjusting the relative position of collimated laser beam 40 in relation to the optical chopper 90 along an axis perpendicular to its axis of rotation (i.e., the vertical axis). The barrier optical density is specific for the treatment wavelength i.e. it allows the aiming beam to pass un-attenuated. It may also block the aiming beam to the same extent as the treatment beam if they originate from the same visible laser source 55. The aiming beam may be attenuated but should still be visible.

Figure 16:
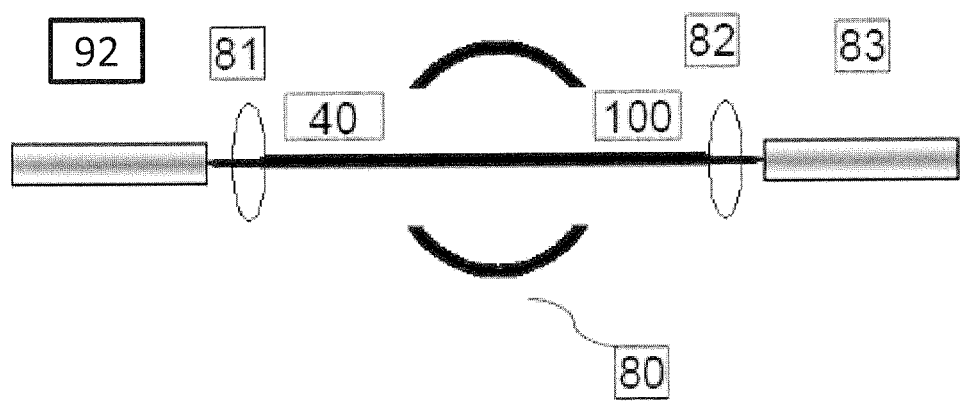
FIG. 16 is a cross-sectional view of an optical chopper disc, in accordance with aspects of the invention.

FIG. 16 shows an example embodiment of the present invention where the optical chopper 90 is used in conjunction with a CW laser system that is not capable of modulating a laser beam. In particular, FIG. 16 shows the optical chopper 90 with a receiving port 92 that receives the laser output from the CW laser system and collimates the laser output, if necessary, using lens 81 to produce a collimated laser beam 40. The rotating disc 80 chops collimated laser beam 40 into a modulated laser beam 100 before it is focused back via lens 82 into output port 83. For example, optical chopper 90 can be connected between the fiber optic port of CW laser system (connected via receiving port 92) and its fiber optic delivery system (connected to the output port 83). Alternatively, it may be placed between the output beam from the laser and targeted tissues. As discussed herein, the frequency and duty cycle can be controlled by the user, via the control panel 8, to change the speed of rotation of the rotating disc 80 and the distance between the center of rotation 30 of the rotating disc 80 and the collimated laser beam 40 passing through the optical chopper 90.

Figure 17:
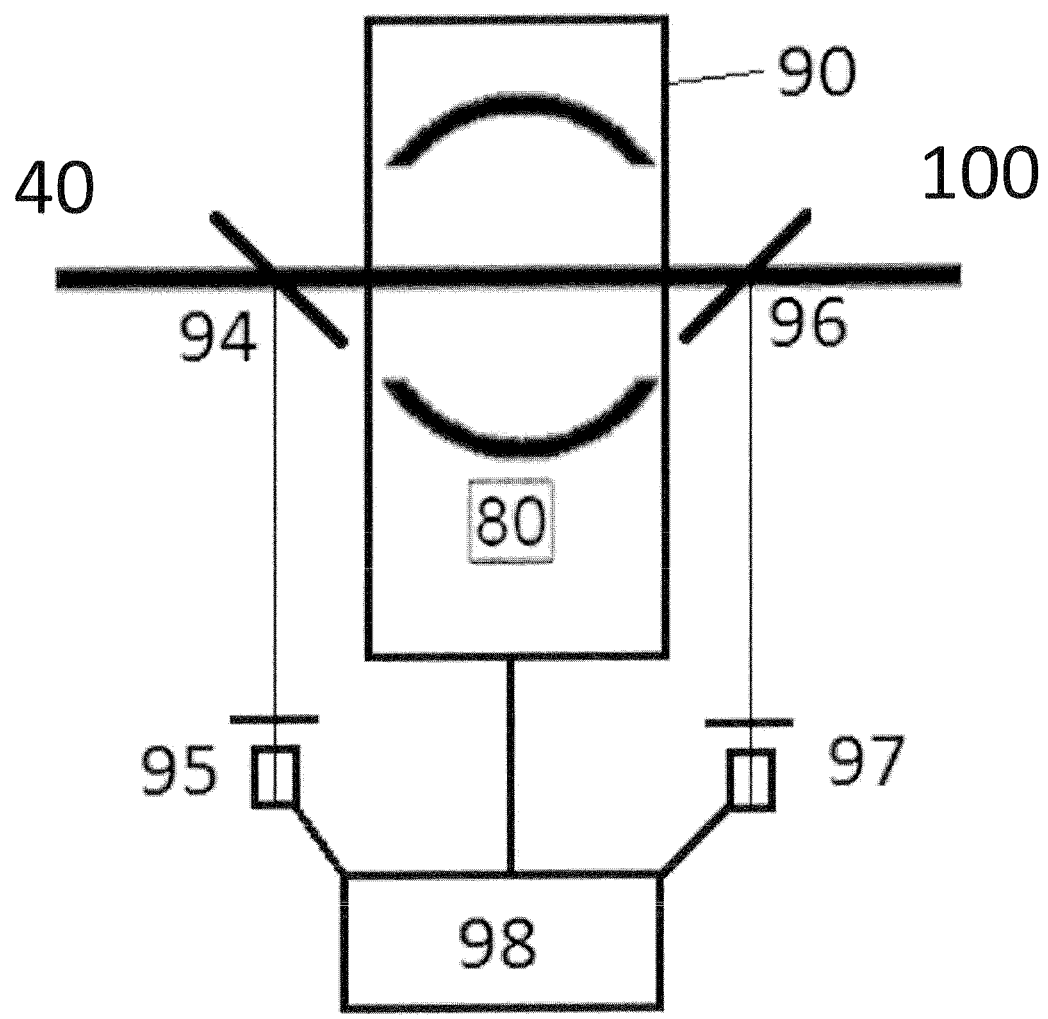
FIG. 17 is a cross-sectional view of compact surgical apparatus with an optical chopper disc, in accordance with aspects of the invention.

FIG. 17 depicts an example embodiment of the optical chopper 90 being used in conjunction with a CW laser system. In accordance with an example embodiment of the present invention, a power level of the collimated laser beam 40 produced by the CW laser system can be adjusted to create an aiming beam and/or a treatment beam. For example, the power level of the collimated laser beam 40 can be adjusted using three power level ranges, namely high (PIII), low (PII), and aiming (PI), to create a high level laser therapy beam, a low level laser therapy beam, and an aiming beam, respectively. In particular, FIG. 17 depicts a path of a collimated laser beam 40 as an aiming power level aiming beam and/or a treatment beam that follow the same path. In accordance with an example operation, the rotating disc 80, in FIG. 17, chops an aiming power level aiming beam into a modulated aiming beam. Additionally, the optical chopper 90 can modulate the aiming beam and the treatment beam to the same parameters (frequency and duty cycle) because the different beam types follow the same path.

In accordance with an example embodiment of the present invention, the aiming beam (e.g., the collimated laser beam 40 at the aiming power level) passes through a beam splitter 94 that reflects a small percentage of the aiming beam towards a detector 95 that includes a diffuser and a photocell. As would be appreciated by one skilled in the art, the photocell of the detector 95 can be configured to measure the sampled aiming beam prior to the aiming beam being chopped by the rotating disc 80. The chopped beam exits the rotating disc 80 as the modulated aiming beam. The modulated aiming beam intersects with another beam splitter 96 that reflects a known small percentage of the modulated aiming beam towards another detector 97. Similar to the detector 95, the photodetector 97 includes a diffuser and a photocell that measures the sampled modulated aiming beam after the aiming beam is chopped by the rotating disc 80. The measurements from photodetectors 95 and 97 can be communicated to an optical chopper controller 98 that computes the actual frequency of beam modulation by measuring the pulse frequency of the modulated aiming beam as measured by the photodetector 97. This allows the controller 98 to adjust the rotation speed of the optical chopper 90 rotating disc 80 to accurately match the required user determined frequency of modulation. Additionally, the controller 98 measures the actual duty cycle by dividing the estimated modulated aiming beam power divided by the estimated CW aiming beam power. As would be appreciated by one skilled in the art, the treatment beam 100 (e.g., the collimated laser beam 40 at the low power or high power level) can be utilized in the same manner. The controller 98 uses the feedback from the photodiodes to measure the actual duty cycle and adjust the placement of the rotating disc 80 to the laser beam path to obtain the desired duty cycle. Similarly, the speed of rotation and resulting duty cycle of the rotating disc 80 are regulated based on feedback from the attenuated aiming beam.

In accordance with an example embodiment of the present invention, the duty cycle can be calculated as follows:

Duty cycle=modulated aiming beam power/$CW$ aiming beam power.

Duty cycle=((detector 97 reading*1/splitter 96 value) *(1-splitter 94 value))/(detector 95 reading*1/ splitter 94 value)

The calculated duty cycle allows the controller 98 to monitor the actual duty cycle and accurately adjust the relative position of rotating disc 80 to the collimated laser beam 40 passing through the optical chopper 90. As would be appreciated by one skilled in the art, the calculated duty cycle can be used to create a hardware feedback loop that is fast and allows delivery of accurate modulation parameters (e.g., power levels, rotation speed of the optical chopper 90, etc.). In accordance with an example embodiment of the present invention, once the collimated laser beam 40 is initiated, the collimated laser beam 40 goes through the optical chopping rotating disc 80 that has optimized parameters from the hardware feedback loop. As a result, the treatment beam 100 passes through the optical chopper 90 at the desired duty rate (as dictated by the controller 98).

As utilized herein, the terms "comprises" and "comprising" are intended to be construed as being inclusive, not exclusive. As utilized herein, the terms "exemplary", "example", and "illustrative", are intended to mean "serving as an example, instance, or illustration" and should not be construed as indicating, or not indicating, a preferred or advantageous configuration relative to other configurations. As utilized herein, the terms "about" and "approximately" are intended to cover variations that may existing in the upper and lower limits of the ranges of subjective or objective values, such as variations in properties, parameters, sizes, and dimensions. In one non-limiting example, the terms "about" and "approximately" mean at, or plus 10 percent or less, or minus 10 percent or less. In one non-limiting example, the terms "about" and "approximately" mean sufficiently close to be deemed by one of skill in the art in the relevant field to be included. As utilized herein, the term "substantially" refers to the complete or nearly complete extend or degree of an action, characteristic, property, state, structure, item, or result, as would be appreciated by one of skill in the art. For example, an object that is "substantially" circular would mean that the object is either completely a circle to mathematically determinable limits, or nearly a circle as would be recognized or understood by one of skill in the art. The exact allowable degree of deviation from absolute completeness may in some instances depend on the specific context. However, in general, the nearness of completion will be so as to have the same overall result as if absolute and total completion were achieved or obtained. The use of "substantially" is equally applicable when utilized in a negative connotation to refer to the complete or near complete lack of an action, characteristic, property, state, structure, item, or result, as would be appreciated by one of skill in the art.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

What is claimed is:

1. A system for modulating a laser beam using an optical chopper, the system comprising:
   the optical chopper comprising at least one rotating disc including at least one barrier and at least one aperture, a motor configured to rotate the at least one rotating disc, a controller configured to adjust placement of the at least one rotating disc relative to a laser beam, and to control a speed of rotation of the at least one rotating disc;
   a laser central processing unit configured to control a laser source configured to generate the laser beam, wherein the laser beam is positioned perpendicular to an axis of rotation of the at least one rotating disc;
   wherein the at least one barrier interrupts the laser beam and the at least one aperture allows the laser beam to pass through the at least one rotating disc uninterrupted to output a high level therapy controlled pulse width train laser beam;
   wherein the high level therapy controlled pulse width train laser beam is controlled by a speed of rotation and distance from a path of the laser beam, perpendicular to the axis of rotation of the at least one rotating disc, to a center of rotation of the at least one rotating disc to mechanically chop the laser beam;
   wherein a variable duty cycle is determined and controlled by adjusting displacement of the at least one rotating disc laterally relative to the path of the laser beam perpendicular to the axis of rotation of the at least one rotating disc; and
   a photodetector and/or feedback current control mechanism configured to measure output power levels of the laser beam for the controller, wherein a speed of rotation and duty cycle of the at least one rotating disc are regulated based on feedback from an attenuated aiming beam.

2. The system of claim 1, wherein the at least one barrier completely blocks the laser beam so that the laser beam peaks at a high therapy power level when the laser beam passes through the at least one rotating disc uninterrupted and is OFF when the at least one barrier interrupts the laser beam.

3. The system of claim 1, wherein the at least one barrier partially blocks the laser beam so that the laser beam peaks at a high therapy power level when the laser beam passes through the at least one rotating disc uninterrupted and alternates to a low-level laser therapy power level when the at least one barrier partially interrupts the laser beam.

4. The system of claim 1, wherein the at least one barrier comprises attenuation barriers of variable size in such a way that adjusting the displacement of the path of the laser beam vertically relative to the at least one rotating disc causes variable attenuation of the laser beam.

5. The system of claim 1, wherein the variable duty cycle is based on the percentage of the angle of rotation in degrees determined and controlled by adjusting displacement laterally, to pass off the center point of rotation, wherein the at least one barrier comprises a first barrier and a second barrier and as the at least one rotating disc continues to rotate the laser beam is initially blocked simultaneously by the second barrier and the first barrier, the laser beam is then blocked only by the first barrier of the at least one rotating disc.

6. The system of claim 5, wherein increasing displacement laterally of the at least one rotating disc relative to the path of the laser beam perpendicular to the axis of rotation of the at least one rotating disc, by shifting the laser beam provided from the laser source or moving the optical chopper, creates more beam de-centration, resulting in smaller duty cycle, enabling continuously variable duty cycles and continuous adjustment of the duty cycle.

7. The system of claim 6, wherein adjusting displacement laterally of the at least one rotating disc relative to the path of the laser beam perpendicular to the axis of rotation of the at least one rotating disc, by shifting the laser beam provided from the laser source or moving the optical chopper, results in the at least one rotating disc being bisected by the laser beam into two asymmetrical halves and the laser beam is chopped at a duty cycle of less than 50% and frequency depending on the rotation speed of the at least one rotating disc.

* * * * *